US007148051B2

(12) United States Patent
Payne et al.

(10) Patent No.: US 7,148,051 B2
(45) Date of Patent: Dec. 12, 2006

(54) PRODUCTION OF 3-HYDROXYCARBOXYLIC ACID USING NITRILASE

(75) Inventors: Mark S. Payne, Wilmington, DE (US); Robert DiCosimo, Rockland, DE (US); Daniel P. O'Keefe, Ridley Park, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 42 days.

(21) Appl. No.: 10/919,182

(22) Filed: Aug. 16, 2004

(65) Prior Publication Data

US 2006/0035352 A1 Feb. 16, 2006

(51) Int. Cl.
 *C12N 9/78* (2006.01)
 *C12N 9/00* (2006.01)
 *C12N 1/20* (2006.01)
 *C07H 21/02* (2006.01)
 *C07H 21/04* (2006.01)

(52) U.S. Cl. .................. 435/227; 435/183; 435/252.3; 435/320.1; 536/23.1; 536/23.2

(58) Field of Classification Search ................ 435/183, 435/227, 252.3, 320.1; 536/23.1, 23.2
See application file for complete search history.

(56) References Cited

U.S. PATENT DOCUMENTS

| 3,553,081 A | 1/1971 | Goodhue et al. |
| 2002/0039970 A1 | 4/2002 | Bramucci et al. |

FOREIGN PATENT DOCUMENTS

| CA | 2103616 | 11/1994 |
| WO | WO 99/29889 | 6/1999 |
| WO | WO 01/75077 A2 | 10/2001 |

OTHER PUBLICATIONS

Bramucci et al. Accession ADU63776. Jan. 27, 2005.*
Michelle L. Gradley et al., Asymmetric Hydrolysis of Chiral Nitriles by *Rhodococcus rhodochrous* NCIMB 11216 Nitrilase, Biotechnology Letters, vol. 16(1):41-46, 1994.
Anna De Raadt et al., Chemoselective Enzymatic Hydrolysis of Aliphatic and Alicyclic Nitriles, J. Chem. Soc. Perkin Trans. 1, pp. 137-140, 1992.
Rebecca A. Cramp et al., Molecular characterisation of a novel thermophilic nitrile hydratase, Biochimica et Biophysica Acta 1431:249-260, 1999.
Carmela Bengis-Garber et al., Selective hydrolysis of dinitriles into cyano-carboxylic acids by *Rhodococcus rhodochrous* N.C.I.B. 11216, Appl. Microbiol. Biotechnol., vol. 32:11-16, 1989.
Brigitte I. Voit et al., Hyperbranched Polyesters, Concise Polymeric Materials Encyclopedia, ed. J.C. Salomone, CRC Press, New York, 1999.

A. Hult et al., Hyperbranched Aliphatic Polyesters, Concise Polymeric Materials Encyclopedia, ed. J.C. Salomone, CRC Press, New York, 1999.
Michihiko Kobayashi et al., Purification and Characterizatin of a Novel Nitrilase of *Rhodococcus rhodochrous* K22 That Acts on Aliphatic Nitriles, Journal of Bacteriology, vol. 172(9):4807-4815, 1990.
Takeshi Sugai et al., Biocatalysis in Organic Synthesis: The Use of Nitrile- and Amide-hydrolyzing Microorganisms, Biosci. Biotech. Biochern., vol. 61(9):1419-1427, 1997.
Tek Chand Bhalla et al., Asymmetric hydrolysis of alpha-aminonitriles to optically active amino acids by a nitrilase of *Rhodococcus rhodochrous* PA-34, Appl. Microbiol. Biotechnol., vol. 37:184-190, 1992.
M. Bayer et al., Synthesis of (S)- and (R)-3-hydroxy acids using cells or purified (S)-3-hydroxycarboxylate oxidoreductase from *Clostridium tyrobutyricum* and the NADP(H) regeneration system of Clostridium thermoaceticum, Appl. Microbiol. Biotechnol., vol. 42:543-547, 1994.
Dieter Seebach et al., Preparation and Structure of Oligolides from (R)-3-Hydroxypentanoic Acid and Comparison with Hydroxybutanoic-Acid Derivatives: A Small Change with Large Consequences, Helvetica Chimica Acta, vol. 77(2007-2034, 1994.
Goodman, Concise Encyclopedia of Polymer Science and Engineering, ed. J.I. Kroschwitz, John Wiley & Sons, New York, pp. 793-799, 1990.
Keizou Yamamoto et al., Purification and Characterization of Nitrilase Responsible for the Enantioselective Hydrolysis from *Acinetobacter* sp. AK 226, Agric. Biol. Chem., vol. 55(6):1459-1466, 1991.
Yasuhisa Asano et al., Degradation of Dinitriles by Fusarium merismoides TG-1*, Agric. Biol. Chem., vol. 44(10):2497-2498, 1980.
Arie Goldlust et al., Induction, Purification, and Characterization of the Nitrilase of Fusarium oxygsporum f. sp. melonis, Biotechnology and Applied Biochemistry, vol. 11:581-601, 1989.
Keizou Yamamoto et al., Purification and Characterization of the Nitrilase from *Alcaligenes faecalis* ATCC 8750 Responsible for Enantioselective Hydrolysis of Mandelonitrile, Journal of Fermentation and Bioengineering, vol. 73(6):425-430, 1992.

(Continued)

*Primary Examiner*—Tekchand Saidha
*Assistant Examiner*—Christian L. Fronda

(57) ABSTRACT

This invention relates to nitrilase mutants having improved nitrilase activity for converting 3-hydroxynitriles to 3-hydroxycarboxylic acids. More specifically, the *Acidovorax facilis* 72W (ATCC 55746) nitrilase gene was mutated using error-prone PCR and site-directed mutagenesis to create nitrilase enzymes having improved nitrilase activity for converting 3-hydroxynitriles (e.g., 3-hydroxybutyronitrile or 3-hydroxyvaleronitrile) to the corresponding 3-hydroxycarboxylic acids. A process using these improved mutants to produce the 3-hydroxycarboxylic acids is also provided.

9 Claims, No Drawings

OTHER PUBLICATIONS

Junzo Hasegawa et al., Production of beta-Hydroxycarboxylic Acids from Aliphatic Carboxylic Acids by Microorganisms*, J. Ferment. Technol., vol. 59(4):257-262, 1981.

Mark J. Burk et al., New Electron-Rich Chiral Phosphones for Asymmetric Catalysis, Organometallics, vol. 9:2653-2655, 1990.

Michihiko Kobayashi et al., Monohydrolysis of an Aliphatic Dinitrile Compound By Nitrilase from *Rhodococcus rhodochrous* K22, Tetrahedron, vol. 46(16):5587-5590, 1990.

Sophie Levy-Schil et al., Aliphatic nitrilase from a soil-isolated *Comamonas testosteroni* sp.:gene cloning and overexpression, purification and primary structure, Gene, vol. 161:15-20, 1995.

John E. Gavagan et al., Chemnoenzymic Production of Lactarns from Aliphatic alpha,w-Dinitriles, J. Org. Chem., vol. 63:4792-4801, 1998.

S. Chauhan et al., Purification, cloning, sequencing and over-expression of *Escherichia coli* of a regioselective aliphatic nitrilase from *Acidovorax facilis* 72W, Appl. Microbiol. Biotechnol., vol. 61:118-122, 2003.

S. Chausan et al., Purification, Cloning, Sequencing and Over-Expression in *Escherichia coli* of a Regioselective Aliphatic Nitrilase from *Acidovorax facilis* 72W, Appl. Microbiol. Biotechnol., 2003, pp. 118-122, vol. 61.

* cited by examiner

SEQUENCE LISTING

<160> NUMBER OF SEQ ID NOS: 18

<210> SEQ ID NO 1
<211> LENGTH: 31
<212> TYPE: DNA
<213> ORGANISM: artificial sequence
<220> FEATURE:
<223> OTHER INFORMATION: Primer

<400> SEQUENCE: 1
gcgcatatgg tttcgtataa cagcaagttc c                                    31

<210> SEQ ID NO 2
<211> LENGTH: 32
<212> TYPE: DNA
<213> ORGANISM: artificial sequence

```
<220> FEATURE:
<223> OTHER INFORMATION: Primer

<400> SEQUENCE: 2
ataggatcct tatggctact ttgctgggac cg                                        32

<210> SEQ ID NO 3
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 3 atg gtt tcg tat aac agc aag ttc ctc gcg gca acc gtt cag gca gag        48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc        96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa       144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag       192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta       240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa       288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat       336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg       384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc       432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt       480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg       528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc       576
Tyr Ser Leu Gly Glu Gln Val His Val Ala Ser Trp Pro Ala Met Ser
            180                 185                 190 cct ctt cag ccg gat gtt ttc caa ctg agc atc gaa gcc aac gcg acg       624
Pro Leu Gln Pro Asp Val Phe Gln Leu Ser Ile Glu Ala Asn Ala Thr
        195                 200                 205 gtc acc cgc tcg tac gca atc gaa ggc caa acc ttt gtg ctt tgc tcg       672
Val Thr Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac       720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac       768
```

```
Glu Gln Arg Ala Leu Leu Pro Gln Gly Cys Gly Trp Ala Arg Ile Tyr
            245                 250                 255 ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
            275                 280                 285 gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
            290                 295                 300 gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca     1104
Thr Lys Leu Phe Glu Gln Ser Leu Leu Ala Glu Glu Pro Val Pro Ala
            355                 360                 365 aag tag                                                              1110
Lys

<210> SEQ ID NO 4
<211> LENGTH: 369
<212> TYPE: PRT
<213> ORGANISM: Acidovorax facilis 72W

<400> SEQUENCE: 4

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
```

-continued

```
                195                 200                 205
Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys

<210> SEQ ID NO 5
<211> LENGTH: 1110
<212> TYPE: DNA
<213> ORGANISM: Artificial sequence
<220> FEATURE:
<223> OTHER INFORMATION: Mutant nitrilase B2 and H9
<220> FEATURE:
<221> NAME/KEY: CDS
<222> LOCATION: (1)..(1110)

<400> SEQUENCE: 5 atg gtt tcg tat aac agc aag ttc ctc gcg gca acc gtt cag gca gag        48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc        96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa       144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag       192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta       240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa       288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat       336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg       384
Leu Ser Gln Val Phe Ile Asp Glu Arg Gly Glu Ile Val Ala Asn Arg
        115                 120                 125
```

```
cgc aag ctg aag ccc aca cac gtt gag cgt acg atc tac ggc gaa ggc      432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt      480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg      528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc      576
Tyr Ser Leu Gly Glu Gln Val His Val Ala Ser Trp Pro Ala Met Ser
            180                 185                 190 cct ctt cag ccg gat gtt ttc caa ctg agc atc gaa gcc aac gcg acg      624
Pro Leu Gln Pro Asp Val Phe Gln Leu Ser Ile Glu Ala Asn Ala Thr
        195                 200                 205 gtc gcc cgc tcg tac gca atc gaa ggc caa acc ttt gtg ctt tgc tcg      672
Val Ala Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
    290                 295                 300 gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca     1104
Thr Lys Leu Phe Glu Gln Ser Leu Leu Ala Glu Glu Pro Val Pro Ala
        355                 360                 365 aag tag                                                             1110
Lys

<210> SEQ ID NO 6
<211> LENGTH: 369
<212> TYPE: PRT
<213> ORGANISM: Artificial sequence
<220> FEATURE:
<223> OTHER INFORMATION: Mutant nitrilase B2 and H9

<400> SEQUENCE: 6

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30
```

```
Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
 50                  55                  60

Tyr Ser Leu Ser Phe Thr Ser Arg Tyr His Glu Asn Ser Leu Glu Leu
 65                  70                  75                  80

Gly Asp Asp Arg Met Arg Arg Leu Gln Leu Ala Ala Arg Arg Asn Lys
                 85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Ala Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Pro Val Pro Ala
        355                 360                 365

Lys

<210> SEQ ID NO 7
<211> LENGTH: 1110
<212> TYPE: DNA
<213> ORGANISM: Artificial sequence
<220> FEATURE:
<223> OTHER INFORMATION: Mutant nitrilase B4
<220> FEATURE:
<221> NAME/KEY: CDS
<222> LOCATION: (1)..(1110)

<400> SEQUENCE: 7 atg gtt tcg tat aac agc aag ttc ctc gcg gca acc gtt cag gca gag      48
```

```
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc        96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa       144
Ile Glu Glu Ala Ala Gln Lys Gly Ala Ser Leu Ile Ala Phe Pro Glu
                35                  40                  45 gta ttc att ccg ggc tac ccc tat tgg gcg tgg ctc ggc gac gtg aag       192
Val Phe Ile Pro Gly Tyr Pro Tyr Trp Ala Trp Leu Gly Asp Val Lys
        50                  55                  60 tgc agc cta agc ttt act tca cgc tat cac gag aat tcg ttg gag cta       240
Cys Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa       288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat       336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg       384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc       432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt       480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag atc atg atg       528
Gly Leu Asn Cys Trp Glu His Phe Gln Pro Leu Ser Lys Ile Met Met
                165                 170                 175 tac agc ctc ggt gag cag gtc cac gtt gca tcg tgg ccg gcg atg tcc       576
Tyr Ser Leu Gly Glu Gln Val His Val Ala Ser Trp Pro Ala Met Ser
            180                 185                 190 cct ctt cag ccg gat gtt ttc caa ctg agc atc gaa gcc aac gcg acg       624
Pro Leu Gln Pro Asp Val Phe Gln Leu Ser Ile Glu Ala Asn Ala Thr
        195                 200                 205 gtc atc cgc tcg tac gca atc gaa ggc caa acc ttt gtg ctt tgc tcg       672
Val Ile Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac       720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac       768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag       816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag       864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg       912
Ala Gly Ala Asp Pro Val Gly His Tyr Ser Arg Pro Asp Val Leu Ser
    290                 295                 300 gtc cag ttc gac ccg cgc aat cat acg cca gtt cat cgc atc ggc att       960
Val Gln Phe Asp Pro Arg Asn His Thr Pro Val His Arg Ile Gly Ile
305                 310                 315                 320
```

-continued

```
gac ggt cgc ttg gat gtg aat acc cgc agt cgc gtg gag aat ttc cga      1008
Asp Gly Arg Leu Asp Val Asn Thr Arg Ser Arg Val Glu Asn Phe Arg
            325                 330                 335 ctg cga caa gcg gct gag cag gag cgt cag gca tcc aag cgg ctc gga      1056
Leu Arg Gln Ala Ala Glu Gln Glu Arg Gln Ala Ser Lys Arg Leu Gly
        340                 345                 350 acg aaa ctc ttt gaa caa tcc ctt ctg gct gaa gaa ccg gtc cca gca      1104
Thr Lys Leu Phe Glu Gln Ser Leu Leu Ala Glu Glu Pro Val Pro Ala
        355                 360                 365 aag tag                                                               1110
Lys
```

<210> SEQ ID NO 8
<211> LENGTH: 369
<212> TYPE: PRT
<213> ORGANISM: Artificial sequence
<220> FEATURE:
<223> OTHER INFORMATION: Mutant nitrilase B4

<400> SEQUENCE: 8

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Cys Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Ile Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Ile Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285
```

```
        Ala Gly Ala Asp Pro Val Gly His Tyr Ser Arg Pro Asp Val Leu Ser
            290                 295                 300

Val Gln Phe Asp Pro Arg Asn His Thr Pro Val His Arg Ile Gly Ile
        305                 310                 315                 320

Asp Gly Arg Leu Asp Val Asn Thr Arg Ser Arg Val Glu Asn Phe Arg
                        325                 330                 335

Leu Arg Gln Ala Ala Glu Gln Arg Gln Ala Ser Lys Arg Leu Gly
                    340                 345                 350

Thr Lys Leu Phe Glu Gln Ser Leu Leu Ala Glu Glu Pro Val Pro Ala
                355                 360                 365

Lys

<210> SEQ ID NO 9
        <211> LENGTH: 42
        <212> TYPE: DNA
        <213> ORGANISM: Artificial sequence
        <220> FEATURE:
        <223> OTHER INFORMATION: Primer

<400> SEQUENCE: 9
cgaagccaac gcgacggtca tgcgctcgta cgcaatcgaa gg                    42

<210> SEQ ID NO 10
        <211> LENGTH: 42
        <212> TYPE: DNA
        <213> ORGANISM: Artificial sequence
        <220> FEATURE:
        <223> OTHER INFORMATION: Primer

<400> SEQUENCE: 10
ccttcgattg cgtacgagcg catgaccgtc gcgttggctt cg                    42

<210> SEQ ID NO 11
        <211> LENGTH: 1110
        <212> TYPE: DNA
        <213> ORGANISM: Artificial sequence
        <220> FEATURE:
        <223> OTHER INFORMATION: Mutant nitrilase with Thr210 to Cys change
        <220> FEATURE:
        <221> NAME/KEY: CDS
        <222> LOCATION: (1)..(1110)

<400> SEQUENCE: 11 atg gtt tcg tat aac agc aag ttc ctc gcg gca acc gtt cag gca gag    48
        Met Val Ser Tyr Asn Ser Lys Phe Leu Ala Ala Thr Val Gln Ala Glu
        1               5                   10                  15 ccg gta tgg ctc gac gca gac gca acg atc gac aag tcg atc ggc atc    96
        Pro Val Trp Leu Asp Ala Asp Ala Thr Ile Asp Lys Ser Ile Gly Ile
                        20                  25                  30 atc gaa gaa gct gcc caa aag ggc gcg agt ctg atc gct ttc ccg gaa   144
        Ile Glu Glu Ala Ala Gln Lys Gly Ala Ser Leu Ile Ala Phe Pro Glu
                    35                  40                  45 gta ttc att ccg ggc tac ccc tat tgg gcg tgg ctc ggc gac gtg aag   192
        Val Phe Ile Pro Gly Tyr Pro Tyr Trp Ala Trp Leu Gly Asp Val Lys
        50                  55                  60 tac agc cta agc ttt act tca cgc tat cac gag aat tcg ttg gag cta   240
        Tyr Ser Leu Ser Phe Thr Ser Arg Tyr His Glu Asn Ser Leu Glu Leu
        65                  70                  75                  80 ggt gac gac cgt atg cgt cgc ctc cag ctg gcc gcg cgc cgc aac aaa   288
        Gly Asp Asp Arg Met Arg Arg Leu Gln Leu Ala Ala Arg Arg Asn Lys
                        85                  90                  95 atc gca ctc gtc atg ggc tat tcg gag cgg gaa gcc gga tcg cgc tat   336
```

-continued

| | | |
|---|---|---|
| Ile Ala Leu Val Met Gly Tyr Ser Glu Arg Glu Ala Gly Ser Arg Tyr<br>                100                        105                    110 | | |
| ctg agc cag gtg ttc atc gac gag cgt ggc gag atc gtt gcc aat cgg<br>Leu Ser Gln Val Phe Ile Asp Glu Arg Gly Glu Ile Val Ala Asn Arg<br>           115                        120                      125 | | 384 |
| cgc aag ctg aag ccc aca cac gtt gag cgt acg atc tac ggc gaa ggc<br>Arg Lys Leu Lys Pro Thr His Val Glu Arg Thr Ile Tyr Gly Glu Gly<br>130                        135                      140 | | 432 |
| aac gga acc gat ttc ctc acg cac gac ttc gcg ttc gga cgc gtc ggt<br>Asn Gly Thr Asp Phe Leu Thr His Asp Phe Ala Phe Gly Arg Val Gly<br>145                      150                      155                      160 | | 480 |
| gga ttg aac tgc tgg gaa cat ttc caa ccg ctc agc aag ttc atg atg<br>Gly Leu Asn Cys Trp Glu His Phe Gln Pro Leu Ser Lys Phe Met Met<br>                      165                      170                    175 | | 528 |
| tac agc ctc ggt gag cag gtc cac gtt gca tcg tgg ccg gcg atg tcc<br>Tyr Ser Leu Gly Glu Gln Val His Val Ala Ser Trp Pro Ala Met Ser<br>                  180                      185                    190 | | 576 |
| cct ctt cag ccg gat gtt ttc caa ctg agc atc gaa gcc aac gcg acg<br>Pro Leu Gln Pro Asp Val Phe Gln Leu Ser Ile Glu Ala Asn Ala Thr<br>           195                      200                    205 | | 624 |
| gtc tgc cgc tcg tac gca atc gaa ggc caa acc ttt gtg ctt tgc tcg<br>Val Cys Arg Ser Tyr Ala Ile Glu Gly Gln Thr Phe Val Leu Cys Ser<br>      210                      215                    220 | | 672 |
| acg cag gtg atc gga cct agc gcg atc gaa acg ttc tgc ctc aac gac<br>Thr Gln Val Ile Gly Pro Ser Ala Ile Glu Thr Phe Cys Leu Asn Asp<br>225                        230                      235                    240 | | 720 |
| gaa cag cgc gca ctg ttg ccg caa gga tgt ggc tgg gcg cgc att tac<br>Glu Gln Arg Ala Leu Leu Pro Gln Gly Cys Gly Trp Ala Arg Ile Tyr<br>                      245                      250                    255 | | 768 |
| ggc ccg gat gga agc gag ctt gcg aag cct ctg gcg gaa gat gct gag<br>Gly Pro Asp Gly Ser Glu Leu Ala Lys Pro Leu Ala Glu Asp Ala Glu<br>                  260                      265                    270 | | 816 |
| ggg atc ttg tac gca gag atc gat ctg gag cag att ctg ctg gcg aag<br>Gly Ile Leu Tyr Ala Glu Ile Asp Leu Glu Gln Ile Leu Leu Ala Lys<br>           275                      280                    285 | | 864 |
| gct gga gcc gat ccg gtc ggg cac tat tcg cgg cct gac gtg ctg tcg<br>Ala Gly Ala Asp Pro Val Gly His Tyr Ser Arg Pro Asp Val Leu Ser<br>           290                      295                    300 | | 912 |
| gtc cag ttc gac ccg cgc aat cat acg cca gtt cat cgc atc ggc att<br>Val Gln Phe Asp Pro Arg Asn His Thr Pro Val His Arg Ile Gly Ile<br>305                        310                      315                    320 | | 960 |
| gac ggt cgc ttg gat gtg aat acc cgc agt cgc gtg gag aat ttc cga<br>Asp Gly Arg Leu Asp Val Asn Thr Arg Ser Arg Val Glu Asn Phe Arg<br>                      325                      330                    335 | | 1008 |
| ctg cga caa gcg gct gag cag gag cgt cag gca tcc aag cgg ctc gga<br>Leu Arg Gln Ala Ala Glu Gln Glu Arg Gln Ala Ser Lys Arg Leu Gly<br>           340                      345                    350 | | 1056 |
| acg aaa ctc ttt gaa caa tcc ctt ctg gct gaa gaa ccg gtc cca gca<br>Thr Lys Leu Phe Glu Gln Ser Leu Leu Ala Glu Glu Pro Val Pro Ala<br>           355                      360                    365 | | 1104 |
| aag tag<br>Lys | | 1110 |

<210> SEQ ID NO 12
<211> LENGTH: 369
<212> TYPE: PRT
<213> ORGANISM: Artificial sequence
<220> FEATURE:
<223> OTHER INFORMATION: Mutant nitrilase with Thr210 to Cys change

<400> SEQUENCE: 12

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
                35                  40                  45

Val Phe Ile Pro Gly Tyr Pro Tyr Trp Ala Trp Leu Gly Asp Val Lys
        50                  55                  60

Tyr Ser Leu Ser Phe Thr Ser Arg Tyr His Glu Asn Ser Leu Glu Leu
65                      70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
                100                 105                 110

Leu Ser Gln Val Phe Ile Asp Glu Arg Gly Glu Ile Val Ala Asn Arg
            115                 120                 125

Arg Lys Leu Lys Pro Thr His Val Glu Arg Thr Ile Tyr Gly Glu Gly
130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
            195                 200                 205

Val Cys Arg Ser Tyr Ala Ile Glu Gly Gln Thr Phe Val Leu Cys Ser
        210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys
```

<210> SEQ ID NO 13
<211> LENGTH: 1110
<212> TYPE: DNA
<213> ORGANISM: Artificial sequence
<220> FEATURE:
<223> OTHER INFORMATION: Mutant nitrilase with Phe168 to Lys change

<220> FEATURE:
<221> NAME/KEY: CDS
<222> LOCATION: (1)..(1110)

<400> SEQUENCE: 13

| | | | | | | | | | | | | | | | | |
|---|---|---|---|---|---|---|---|---|---|---|---|---|---|---|---|---|
| atg | gtt | tcg | tat | aac | agc | aag | ttc | ctc | gcg | gca | acc | gtt | cag | gca | gag | 48 |
| Met | Val | Ser | Tyr | Asn | Ser | Lys | Phe | Leu | Ala | Ala | Thr | Val | Gln | Ala | Glu | |
| 1 | | | | 5 | | | | | 10 | | | | | 15 | | |
| ccg | gta | tgg | ctc | gac | gca | gac | gca | acg | atc | gac | aag | tcg | atc | ggc | atc | 96 |
| Pro | Val | Trp | Leu | Asp | Ala | Asp | Ala | Thr | Ile | Asp | Lys | Ser | Ile | Gly | Ile | |
| | | | 20 | | | | | 25 | | | | | 30 | | | |
| atc | gaa | gaa | gct | gcc | caa | aag | ggc | gcg | agt | ctg | atc | gct | ttc | ccg | gaa | 144 |
| Ile | Glu | Glu | Ala | Ala | Gln | Lys | Gly | Ala | Ser | Leu | Ile | Ala | Phe | Pro | Glu | |
| | | 35 | | | | | 40 | | | | | 45 | | | | |
| gta | ttc | att | ccg | ggc | tac | ccc | tat | tgg | gcg | tgg | ctc | ggc | gac | gtg | aag | 192 |
| Val | Phe | Ile | Pro | Gly | Tyr | Pro | Tyr | Trp | Ala | Trp | Leu | Gly | Asp | Val | Lys | |
| | 50 | | | | | 55 | | | | | 60 | | | | | |
| tac | agc | cta | agc | ttt | act | tca | cgc | tat | cac | gag | aat | tcg | ttg | gag | cta | 240 |
| Tyr | Ser | Leu | Ser | Phe | Thr | Ser | Arg | Tyr | His | Glu | Asn | Ser | Leu | Glu | Leu | |
| 65 | | | | | 70 | | | | | 75 | | | | | 80 | |
| ggt | gac | gac | cgt | atg | cgt | cgc | ctc | cag | ctg | gcc | gcg | cgc | cgc | aac | aaa | 288 |
| Gly | Asp | Asp | Arg | Met | Arg | Arg | Leu | Gln | Leu | Ala | Ala | Arg | Arg | Asn | Lys | |
| | | | | 85 | | | | | 90 | | | | | 95 | | |
| atc | gca | ctc | gtc | atg | ggc | tat | tcg | gag | cgg | gaa | gcc | gga | tcg | cgc | tat | 336 |
| Ile | Ala | Leu | Val | Met | Gly | Tyr | Ser | Glu | Arg | Glu | Ala | Gly | Ser | Arg | Tyr | |
| | | | 100 | | | | | 105 | | | | | 110 | | | |
| ctg | agc | cag | gtg | ttc | atc | gac | gag | cgt | ggc | gag | atc | gtt | gcc | aat | cgg | 384 |
| Leu | Ser | Gln | Val | Phe | Ile | Asp | Glu | Arg | Gly | Glu | Ile | Val | Ala | Asn | Arg | |
| | | 115 | | | | | 120 | | | | | 125 | | | | |
| cgc | aag | ctg | aag | ccc | aca | cac | gtt | gag | cgt | acg | atc | tac | ggc | gaa | ggc | 432 |
| Arg | Lys | Leu | Lys | Pro | Thr | His | Val | Glu | Arg | Thr | Ile | Tyr | Gly | Glu | Gly | |
| | 130 | | | | | 135 | | | | | 140 | | | | | |
| aac | gga | acc | gat | ttc | ctc | acg | cac | gac | ttc | gcg | ttc | gga | cgc | gtc | ggt | 480 |
| Asn | Gly | Thr | Asp | Phe | Leu | Thr | His | Asp | Phe | Ala | Phe | Gly | Arg | Val | Gly | |
| 145 | | | | | 150 | | | | | 155 | | | | | 160 | |
| gga | ttg | aac | tgc | tgg | gaa | cat | aaa | caa | ccg | ctc | agc | aag | ttc | atg | atg | 528 |
| Gly | Leu | Asn | Cys | Trp | Glu | His | Lys | Gln | Pro | Leu | Ser | Lys | Phe | Met | Met | |
| | | | | 165 | | | | | 170 | | | | | 175 | | |
| tac | agc | ctc | ggt | gag | cag | gtc | cac | gtt | gca | tcg | tgg | ccg | gcg | atg | tcc | 576 |
| Tyr | Ser | Leu | Gly | Glu | Gln | Val | His | Val | Ala | Ser | Trp | Pro | Ala | Met | Ser | |
| | | | 180 | | | | | 185 | | | | | 190 | | | |
| cct | ctt | cag | ccg | gat | gtt | ttc | caa | ctg | agc | atc | gaa | gcc | aac | gcg | acg | 624 |
| Pro | Leu | Gln | Pro | Asp | Val | Phe | Gln | Leu | Ser | Ile | Glu | Ala | Asn | Ala | Thr | |
| | | 195 | | | | | 200 | | | | | 205 | | | | |
| gtc | acc | cgc | tcg | tac | gca | atc | gaa | ggc | caa | acc | ttt | gtg | ctt | tgc | tcg | 672 |
| Val | Thr | Arg | Ser | Tyr | Ala | Ile | Glu | Gly | Gln | Thr | Phe | Val | Leu | Cys | Ser | |
| | 210 | | | | | 215 | | | | | 220 | | | | | |
| acg | cag | gtg | atc | gga | cct | agc | gcg | atc | gaa | acg | ttc | tgc | ctc | aac | gac | 720 |
| Thr | Gln | Val | Ile | Gly | Pro | Ser | Ala | Ile | Glu | Thr | Phe | Cys | Leu | Asn | Asp | |
| 225 | | | | | 230 | | | | | 235 | | | | | 240 | |
| gaa | cag | cgc | gca | ctg | ttg | ccg | caa | gga | tgt | ggc | tgg | gcg | cgc | att | tac | 768 |
| Glu | Gln | Arg | Ala | Leu | Leu | Pro | Gln | Gly | Cys | Gly | Trp | Ala | Arg | Ile | Tyr | |
| | | | | 245 | | | | | 250 | | | | | 255 | | |
| ggc | ccg | gat | gga | agc | gag | ctt | gcg | aag | cct | ctg | gcg | gaa | gat | gct | gag | 816 |
| Gly | Pro | Asp | Gly | Ser | Glu | Leu | Ala | Lys | Pro | Leu | Ala | Glu | Asp | Ala | Glu | |
| | | | 260 | | | | | 265 | | | | | 270 | | | |
| ggg | atc | ttg | tac | gca | gag | atc | gat | ctg | gag | cag | att | ctg | ctg | gcg | aag | 864 |
| Gly | Ile | Leu | Tyr | Ala | Glu | Ile | Asp | Leu | Glu | Gln | Ile | Leu | Leu | Ala | Lys | |
| | | 275 | | | | | 280 | | | | | 285 | | | | |
| gct | gga | gcc | gat | ccg | gtc | ggg | cac | tat | tcg | cgg | cct | gac | gtg | ctg | tcg | 912 |

```
Ala Gly Ala Asp Pro Val Gly His Tyr Ser Arg Pro Asp Val Leu Ser
        290                 295                 300 gtc cag ttc gac ccg cgc aat cat acg cca gtt cat cgc atc ggc att        960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga       1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga       1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca       1104
Thr Lys Leu Phe Glu Gln Ser Leu Leu Ala Glu Glu Pro Val Pro Ala
        355                 360                 365 aag tag                                                                1110
Lys

<210> SEQ ID NO 14
<211> LENGTH: 369
<212> TYPE: PRT
<213> ORGANISM: Artificial sequence
<220> FEATURE:
<223> OTHER INFORMATION: Mutant nitrilase with Phe168 to Lys change

<400> SEQUENCE: 14

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Lys Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255
```

```
Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
            275                 280                 285

Ala Gly Ala Asp Pro Val Gly His Tyr Ser Arg Pro Asp Val Leu Ser
            290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Arg Gln Ala Ser Lys Arg Leu Gly
            340                 345                 350

Thr Lys Leu Phe Glu Gln Ser Leu Leu Ala Glu Pro Val Pro Ala
            355                 360                 365

Lys
```

<210> SEQ ID NO 15
<211> LENGTH: 1110
<212> TYPE: DNA
<213> ORGANISM: Artificial sequence
<220> FEATURE:
<223> OTHER INFORMATION: Mutant nitrilase with Phe168 to Val change
<220> FEATURE:
<221> NAME/KEY: CDS
<222> LOCATION: (1)..(1110)

<400> SEQUENCE: 15

```
atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
                20                  25                  30 atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
            35                  40                  45 gta ttc att ccg ggc tac ccc tat tgg gcg tgg ctc ggc gac gtg aag     192
Val Phe Ile Pro Gly Tyr Pro Tyr Trp Ala Trp Leu Gly Asp Val Lys
        50                  55                  60 tac agc cta agc ttt act tca cgc tat cac gag aat tcg ttg gag cta     240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa     288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat     336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg     384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc     432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt     480
Asn Gly Thr Asp Phe Leu Thr His Asp Phe Ala Phe Gly Arg Val Gly
145                 150                 155                 160 gga ttg aac tgc tgg gaa cat gtt caa ccg ctc agc aag ttc atg atg     528
Gly Leu Asn Cys Trp Glu His Val Gln Pro Leu Ser Lys Phe Met Met
```

|  |  |  |  |  |  |  |  |  |  |  |  |  |  |  |  |
|---|---|---|---|---|---|---|---|---|---|---|---|---|---|---|---|
|  |  |  | 165 |  |  |  | 170 |  |  |  | 175 |  |  |  |  |
| tac | agc | ctc | ggt | gag | cag | gtc | cac | gtt | gca | tcg | tgg | ccg | gcg | atg | tcc | 576 |
| Tyr | Ser | Leu | Gly | Glu | Gln | Val | His | Val | Ala | Ser | Trp | Pro | Ala | Met | Ser |  |
|  |  |  | 180 |  |  |  | 185 |  |  |  | 190 |  |  |  |  |
| cct | ctt | cag | ccg | gat | gtt | ttc | caa | ctg | agc | atc | gaa | gcc | aac | gcg | acg | 624 |
| Pro | Leu | Gln | Pro | Asp | Val | Phe | Gln | Leu | Ser | Ile | Glu | Ala | Asn | Ala | Thr |  |
|  |  |  | 195 |  |  |  | 200 |  |  |  | 205 |  |  |  |  |
| gtc | acc | cgc | tcg | tac | gca | atc | gaa | ggc | caa | acc | ttt | gtg | ctt | tgc | tcg | 672 |
| Val | Thr | Arg | Ser | Tyr | Ala | Ile | Glu | Gly | Gln | Thr | Phe | Val | Leu | Cys | Ser |  |
|  | 210 |  |  |  |  | 215 |  |  |  |  | 220 |  |  |  |  |
| acg | cag | gtg | atc | gga | cct | agc | gcg | atc | gaa | acg | ttc | tgc | ctc | aac | gac | 720 |
| Thr | Gln | Val | Ile | Gly | Pro | Ser | Ala | Ile | Glu | Thr | Phe | Cys | Leu | Asn | Asp |  |
| 225 |  |  |  |  | 230 |  |  |  |  | 235 |  |  |  |  | 240 |
| gaa | cag | cgc | gca | ctg | ttg | ccg | caa | gga | tgt | ggc | tgg | gcg | cgc | att | tac | 768 |
| Glu | Gln | Arg | Ala | Leu | Leu | Pro | Gln | Gly | Cys | Gly | Trp | Ala | Arg | Ile | Tyr |  |
|  |  |  |  |  | 245 |  |  |  |  | 250 |  |  |  |  | 255 |
| ggc | ccg | gat | gga | agc | gag | ctt | gcg | aag | cct | ctg | gcg | gaa | gat | gct | gag | 816 |
| Gly | Pro | Asp | Gly | Ser | Glu | Leu | Ala | Lys | Pro | Leu | Ala | Glu | Asp | Ala | Glu |  |
|  |  |  | 260 |  |  |  |  | 265 |  |  |  |  | 270 |  |  |
| ggg | atc | ttg | tac | gca | gag | atc | gat | ctg | gag | cag | att | ctg | ctg | gcg | aag | 864 |
| Gly | Ile | Leu | Tyr | Ala | Glu | Ile | Asp | Leu | Glu | Gln | Ile | Leu | Leu | Ala | Lys |  |
|  |  | 275 |  |  |  |  | 280 |  |  |  |  | 285 |  |  |  |
| gct | gga | gcc | gat | ccg | gtc | ggg | cac | tat | tcg | cgg | cct | gac | gtg | ctg | tcg | 912 |
| Ala | Gly | Ala | Asp | Pro | Val | Gly | His | Tyr | Ser | Arg | Pro | Asp | Val | Leu | Ser |  |
| 290 |  |  |  |  | 295 |  |  |  |  | 300 |  |  |  |  |  |
| gtc | cag | ttc | gac | ccg | cgc | aat | cat | acg | cca | gtt | cat | cgc | atc | ggc | att | 960 |
| Val | Gln | Phe | Asp | Pro | Arg | Asn | His | Thr | Pro | Val | His | Arg | Ile | Gly | Ile |  |
| 305 |  |  |  |  | 310 |  |  |  |  | 315 |  |  |  |  | 320 |
| gac | ggt | cgc | ttg | gat | gtg | aat | acc | cgc | agt | cgc | gtg | gag | aat | ttc | cga | 1008 |
| Asp | Gly | Arg | Leu | Asp | Val | Asn | Thr | Arg | Ser | Arg | Val | Glu | Asn | Phe | Arg |  |
|  |  |  |  | 325 |  |  |  |  | 330 |  |  |  |  | 335 |  |
| ctg | cga | caa | gcg | gct | gag | cag | gag | cgt | cag | gca | tcc | aag | cgg | ctc | gga | 1056 |
| Leu | Arg | Gln | Ala | Ala | Glu | Gln | Glu | Arg | Gln | Ala | Ser | Lys | Arg | Leu | Gly |  |
|  |  |  | 340 |  |  |  |  | 345 |  |  |  |  | 350 |  |  |
| acg | aaa | ctc | ttt | gaa | caa | tcc | ctt | ctg | gct | gaa | gaa | ccg | gtc | cca | gca | 1104 |
| Thr | Lys | Leu | Phe | Glu | Gln | Ser | Leu | Leu | Ala | Glu | Glu | Pro | Val | Pro | Ala |  |
|  |  | 355 |  |  |  |  | 360 |  |  |  |  | 365 |  |  |  |
| aag | tag |  |  |  |  |  |  |  |  |  |  |  |  |  |  | 1110 |
| Lys |  |  |  |  |  |  |  |  |  |  |  |  |  |  |  |  |

<210> SEQ ID NO 16
<211> LENGTH: 369
<212> TYPE: PRT
<213> ORGANISM: Artificial sequence
<220> FEATURE:
<223> OTHER INFORMATION: Mutant nitrilase with Phe168 to Val change

<400> SEQUENCE: 16

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys

-continued

```
                            85                  90                  95
Ile Ala Leu Val Met Gly Tyr Ser Glu Arg Glu Ala Gly Ser Arg Tyr
                100                 105                 110

Leu Ser Gln Val Phe Ile Asp Glu Arg Gly Glu Ile Val Ala Asn Arg
            115                 120                 125

Arg Lys Leu Lys Pro Thr His Val Glu Arg Thr Ile Tyr Gly Glu Gly
        130                 135                 140

Asn Gly Thr Asp Phe Leu Thr His Asp Phe Ala Phe Gly Arg Val Gly
145                 150                 155                 160

Gly Leu Asn Cys Trp Glu His Val Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys
```

```
<210> SEQ ID NO 17
<211> LENGTH: 1110
<212> TYPE: DNA
<213> ORGANISM: Artificial sequence
<220> FEATURE:
<223> OTHER INFORMATION: Mutant nitrilase with Phe168 to Leu change
<220> FEATURE:
<221> NAME/KEY: CDS
<222> LOCATION: (1)..(1110)

<400> SEQUENCE: 17
```

```
atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
        35                  40                  45
```

-continued

| | |
|---|---|
| gta ttc att ccg ggc tac ccc tat tgg gcg tgg ctc ggc gac gtg aag<br>Val Phe Ile Pro Gly Tyr Pro Tyr Trp Ala Trp Leu Gly Asp Val Lys<br>50                           55                             60 | 192 |
| tac agc cta agc ttt act tca cgc tat cac gag aat tcg ttg gag cta<br>Tyr Ser Leu Ser Phe Thr Ser Arg Tyr His Glu Asn Ser Leu Glu Leu<br>65                           70                           75                           80 | 240 |
| ggt gac gac cgt atg cgt cgc ctc cag ctg gcc gcg cgc cgc aac aaa<br>Gly Asp Asp Arg Met Arg Arg Leu Gln Leu Ala Ala Arg Arg Asn Lys<br>                         85                           90                           95 | 288 |
| atc gca ctc gtc atg ggc tat tcg gag cgg gaa gcc gga tcg cgc tat<br>Ile Ala Leu Val Met Gly Tyr Ser Glu Arg Glu Ala Gly Ser Arg Tyr<br>               100                      105                      110 | 336 |
| ctg agc cag gtg ttc atc gac gag cgt ggc gag atc gtt gcc aat cgg<br>Leu Ser Gln Val Phe Ile Asp Glu Arg Gly Glu Ile Val Ala Asn Arg<br>           115                      120                      125 | 384 |
| cgc aag ctg aag ccc aca cac gtt gag cgt acg atc tac ggc gaa ggc<br>Arg Lys Leu Lys Pro Thr His Val Glu Arg Thr Ile Tyr Gly Glu Gly<br>130                         135                      140 | 432 |
| aac gga acc gat ttc ctc acg cac gac ttc gcg ttc gga cgc gtc ggt<br>Asn Gly Thr Asp Phe Leu Thr His Asp Phe Ala Phe Gly Arg Val Gly<br>145                         150                      155                      160 | 480 |
| gga ttg aac tgc tgg gaa cat cta caa ccg ctc agc aag ttc atg atg<br>Gly Leu Asn Cys Trp Glu His Leu Gln Pro Leu Ser Lys Phe Met Met<br>               165                      170                      175 | 528 |
| tac agc ctc ggt gag cag gtc cac gtt gca tcg tgg ccg gcg atg tcc<br>Tyr Ser Leu Gly Glu Gln Val His Val Ala Ser Trp Pro Ala Met Ser<br>           180                      185                      190 | 576 |
| cct ctt cag ccg gat gtt ttc caa ctg agc atc gaa gcc aac gcg acg<br>Pro Leu Gln Pro Asp Val Phe Gln Leu Ser Ile Glu Ala Asn Ala Thr<br>           195                      200                      205 | 624 |
| gtc acc cgc tcg tac gca atc gaa ggc caa acc ttt gtg ctt tgc tcg<br>Val Thr Arg Ser Tyr Ala Ile Glu Gly Gln Thr Phe Val Leu Cys Ser<br>           210                      215                      220 | 672 |
| acg cag gtg atc gga cct agc gcg atc gaa acg ttc tgc ctc aac gac<br>Thr Gln Val Ile Gly Pro Ser Ala Ile Glu Thr Phe Cys Leu Asn Asp<br>225                         230                      235                      240 | 720 |
| gaa cag cgc gca ctg ttg ccg caa gga tgt ggc tgg gcg cgc att tac<br>Glu Gln Arg Ala Leu Leu Pro Gln Gly Cys Gly Trp Ala Arg Ile Tyr<br>                         245                      250                      255 | 768 |
| ggc ccg gat gga agc gag ctt gcg aag cct ctg gcg gaa gat gct gag<br>Gly Pro Asp Gly Ser Glu Leu Ala Lys Pro Leu Ala Glu Asp Ala Glu<br>           260                      265                      270 | 816 |
| ggg atc ttg tac gca gag atc gat ctg gag cag att ctg ctg gcg aag<br>Gly Ile Leu Tyr Ala Glu Ile Asp Leu Glu Gln Ile Leu Leu Ala Lys<br>           275                      280                      285 | 864 |
| gct gga gcc gat ccg gtc ggg cac tat tcg cgg cct gac gtg ctg tcg<br>Ala Gly Ala Asp Pro Val Gly His Tyr Ser Arg Pro Asp Val Leu Ser<br>290                         295                      300 | 912 |
| gtc cag ttc gac ccg cgc aat cat acg cca gtt cat cgc atc ggc att<br>Val Gln Phe Asp Pro Arg Asn His Thr Pro Val His Arg Ile Gly Ile<br>305                         310                      315                      320 | 960 |
| gac ggt cgc ttg gat gtg aat acc cgc agt cgc gtg gag aat ttc cga<br>Asp Gly Arg Leu Asp Val Asn Thr Arg Ser Arg Val Glu Asn Phe Arg<br>                         325                      330                      335 | 1008 |
| ctg cga caa gcg gct gag cag gag cgt cag gca tcc aag cgg ctc gga<br>Leu Arg Gln Ala Ala Glu Gln Glu Arg Gln Ala Ser Lys Arg Leu Gly<br>           340                      345                      350 | 1056 |
| acg aaa ctc ttt gaa caa tcc ctt ctg gct gaa gaa ccg tcc cca gca<br>Thr Lys Leu Phe Glu Gln Ser Leu Leu Ala Glu Glu Pro Val Pro Ala | 1104 | aag tag                                                                  1110
Lys <210> SEQ ID NO 18
<211> LENGTH: 369
<212> TYPE: PRT
<213> ORGANISM: Artificial sequence
<220> FEATURE:
<223> OTHER INFORMATION: Mutant nitrilase with Phe168 to Leu change

<400> SEQUENCE: 18

```
Met Val Ser Tyr Asn Ser Lys Phe Leu Ala Ala Thr Val Gln Ala Glu
1               5                   10                  15
Pro Val Trp Leu Asp Ala Asp Ala Thr Ile Asp Lys Ser Ile Gly Ile
            20                  25                  30
Ile Glu Glu Ala Ala Gln Lys Gly Ala Ser Leu Ile Ala Phe Pro Glu
        35                  40                  45
Val Phe Ile Pro Gly Tyr Pro Tyr Trp Ala Trp Leu Gly Asp Val Lys
    50                  55                  60
Tyr Ser Leu Ser Phe Thr Ser Arg Tyr His Glu Asn Ser Leu Glu Leu
65                  70                  75                  80
Gly Asp Asp Arg Met Arg Arg Leu Gln Leu Ala Ala Arg Arg Asn Lys
                85                  90                  95
Ile Ala Leu Val Met Gly Tyr Ser Glu Arg Glu Ala Gly Ser Arg Tyr
            100                 105                 110
Leu Ser Gln Val Phe Ile Asp Glu Arg Gly Glu Ile Val Ala Asn Arg
        115                 120                 125
Arg Lys Leu Lys Pro Thr His Val Glu Arg Thr Ile Tyr Gly Glu Gly
    130                 135                 140
Asn Gly Thr Asp Phe Leu Thr His Asp Phe Ala Phe Gly Arg Val Gly
145                 150                 155                 160
Gly Leu Asn Cys Trp Glu His Leu Gln Pro Leu Ser Lys Phe Met Met
                165                 170                 175
Tyr Ser Leu Gly Glu Gln Val His Val Ala Ser Trp Pro Ala Met Ser
            180                 185                 190
Pro Leu Gln Pro Asp Val Phe Gln Leu Ser Ile Glu Ala Asn Ala Thr
        195                 200                 205
Val Thr Arg Ser Tyr Ala Ile Glu Gly Gln Thr Phe Val Leu Cys Ser
    210                 215                 220
Thr Gln Val Ile Gly Pro Ser Ala Ile Glu Thr Phe Cys Leu Asn Asp
225                 230                 235                 240
Glu Gln Arg Ala Leu Leu Pro Gln Gly Cys Gly Trp Ala Arg Ile Tyr
                245                 250                 255
Gly Pro Asp Gly Ser Glu Leu Ala Lys Pro Leu Ala Glu Asp Ala Glu
            260                 265                 270
Gly Ile Leu Tyr Ala Glu Ile Asp Leu Glu Gln Ile Leu Leu Ala Lys
        275                 280                 285
Ala Gly Ala Asp Pro Val Gly His Tyr Ser Arg Pro Asp Val Leu Ser
    290                 295                 300
Val Gln Phe Asp Pro Arg Asn His Thr Pro Val His Arg Ile Gly Ile
305                 310                 315                 320
Asp Gly Arg Leu Asp Val Asn Thr Arg Ser Arg Val Glu Asn Phe Arg
                325                 330                 335
Leu Arg Gln Ala Ala Glu Gln Glu Arg Gln Ala Ser Lys Arg Leu Gly
```

```
                340             345             350
Thr Lys Leu Phe Glu Gln Ser Leu Leu Ala Glu Glu Pro Val Pro Ala
        355             360             365
Lys
```

PRODUCTION OF 3-HYDROXYCARBOXYLIC ACID USING NITRILASE

FIELD OF THE INVENTION

This invention relates to the field of microbiology.

BACKGROUND OF THE INVENTION

New polymers with superior performance, unique properties, improved cost effectiveness, quality, and low ecological impact are of ongoing interest to industry. In particular, functional polymers having branched, compact structures and terminally located reactive groups are in demand because of their lower inherent viscosity and higher reactivity as compared to conventional linear statistical co-polymers.

Such superior polymers can be prepared by copolymerizing hyperbranching hydroxycarboxylic acid comonomers (hyperbranching $AB_n$ type, where A and B are moieties with hydroxyl- or carboxyl-derived reactive groups, n is 2 or more) (Hult et al., pp. 656–658 and Voit et al., pp. 658–659 in *Concise Polymeric Materials Encyclopedia*, ed. J. C. Salomone, CRC Press, New York, 1999) and a variety of linear hydroxycarboxylic acid comonomers (linear AB type), including 3-hydroxyvaleric acid (3-HVA) and 3-hydroxybutyric acid (3-HBA).

3-Hydroxycarboxylic acid is useful as a (co)monomer for making linear polyesters. Polyesters are useful as thermoplastic, thermoset, semicrystalline, amorphous, rigid, and elastomeric materials. They are the basis of fibers, films, moldings, and coatings (Goodman, pp. 793–799 in *Concise Encyclopedia of Polymer Science and Engineering*, ed. J. I. Kroschwitz, John Wiley & Sons, New York, 1990).

3-Hydroxyvaleric acid has been prepared by the 3-hydroxylation of valeric acid in fermentation using *Candida rugosa* (Hasegawa et al., *J. Ferment. Technol.* 59:257–262 (1981); JP 59053838 B4), and a single enantiomer of 3-hydroxyvaleric acid was similarly prepared by fermentative 3-hydroxylation of valeric acid with *Pseudomonas putida*, *Pseudomonas fluorescens*, *Arthrobacter oxydans* and *Arthrobacter crystallopietes* (U.S. Pat. No. 3,553,081). These methods for fermentative oxidation of valeric acid typically produce 3-hydroxyvaleric acid at low product concentrations, and require an elaborate and expensive separation of 3-hydroxyvaleric acid from the fermentation broth. (R)-(-)-3-Hydroxyvaleric acid has been prepared by the chemical degradation (Seebach et al., *Helv. Chim. Acta* 77:2007–2034 (1994)) or by fermentative autodegradation (WO 9929889) of poly(3-hydroxybutyrate/3-hydroxyvalerate), but degradation of hydroxybutyric acid/hydroxyvaleric acid copolymers also requires a difficult separation of 3-hydroxybutyric acid from the co-product 3-hydroxyvaleric acid. (R)-(-)-3-Hydroxyvaleric acid has also been prepared by the enzymatic reduction of 3-oxovaleric acid (Bayer et al., *Appl. Microbiol. Biotechnol.* 42:543–547 (1994)) or by the asymmetric hydrogenation of methyl 3-oxovalerate followed by saponification (Burk et al., *Organometallics* 9:2653–2655 (1990)).

Nitriles are readily converted to the corresponding carboxylic acids by a variety of chemical processes. These processes typically require strongly acidic or basic reaction conditions and high reaction temperatures, and usually produce unwanted byproducts and/or large amounts of inorganic salts as unwanted waste. Reaction conditions for the chemical hydrolysis of nitriles that additionally have a hydroxyl group, such as for the conversion of 3-hydroxyvaleronitrile to 3-hydroxyvaleric acid, will usually result in the undesirable elimination of primary, secondary, or tertiary hydroxyl groups to produce carbon-carbon double bonds.

The enzyme-catalyzed hydrolysis of nitriles to the corresponding carboxylic acids is often preferred to chemical methods, since the reactions are often run at ambient temperature, do not require strongly acidic or basic reaction conditions, and produce the desired product with high selectivity at high conversion. A combination of two enzymes, nitrile hydratase and amidase, can be used to convert aliphatic nitriles to the corresponding carboxylic acid in aqueous solution. The aliphatic nitrile is initially converted to an amide by the nitrile hydratase, then the amide is subsequently converted by the amidase to the corresponding carboxylic acid. A wide variety of bacterial genera are known to possess a diverse spectrum of nitrile hydratase and amidase activities (Sugai et al., *Biosci. Biotech. Biochem.* 61:1419–1427 (1997)), including *Rhodococcus*, *Pseudomonas*, *Alcaligenes*, *Arthrobacter*, *Bacillus*, *Bacteridium*, *Brevibacterium*, *Corynebacterium* and *Micrococcus*. The fungus *Fusarium merismoides* TG-1 has also been used as catalyst for the hydrolysis of aliphatic nitriles and dinitriles (Asano et al., *Agric. Biol. Chem.* 44:2497–2498 (1980)). Immobilized nitrile hydratase and amidase from *Rhodococcus* sp. (SP409 from Novo Industri) was used to hydrolyze 3-hydroxypropionitrile, 3-hydroxyheptanenitrile, and 3-hydroxynonanenitrile to the corresponding 3-hydroxycarboxylic acids in 63%, 62% and 83% yields, respectively (de Raadt et al., *J. Chem. Soc.* Perkin Trans. 1, 137–140 (1992)). The formation of the corresponding amide was also observed by TLC. In contrast, the purified nitrile hydratase of *Bacillus pallidus* Dac521 hydrolyzed a variety of aliphatic nitriles, but did not hydrolyze 3-hydroxy-propionitrile (Cramp et al., *Biochim. Biophys. Acta* 1431:249–260 (1999)).

A single enzyme, nitrilase, also converts a nitrile to the corresponding carboxylic acid and ammonia in aqueous solution, but without the intermediate formation of an amide (Equations 1 and 2).

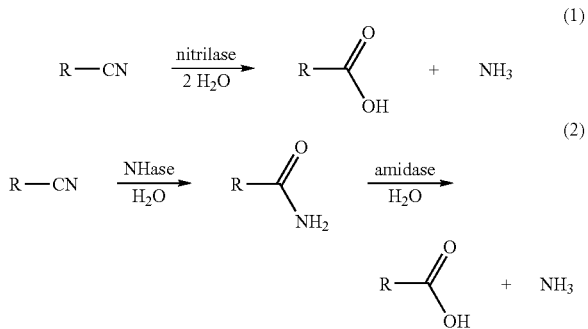

Kobayashi et al. (*Tetrahedron* 46:5587–5590 (1990) and *J. Bacteriology* 172:4807–4815 (1990)) have described an aliphatic nitrilase isolated from *Rhodococcus rhodochrous* K22 which catalyzed the hydrolysis of a variety of aliphatic nitriles to the corresponding carboxylic acids. A nitrilase from *Comamonas testosteroni* has been isolated that can convert a range of aliphatic α,ω-dinitriles to either the corresponding ω-cyanocarboxylic acids or dicarboxylic acids (CA 2,103,616; Lévy-Schil et al., *Gene* 161:15–20 (1995)). Aliphatic nitrilases are also produced by *Rhodococcus rhodochrous* NCIMB 11216 (Bengis-Garber et al.,

*Appl. Microbiol. Biotechnol.* 32:11–16 (1989); Gradley et al., *Biotechnology Lett.* 16:41–46 (1994)), *Rhodococcus rhodochrous* PA-34 (Bhalla et al., *Appl. Microbiol. Biotechnol.* 37:184–190 (1992)), *Fusarium oxysporum* f. sp. *melonis* (Goldlust et al., *Biotechnol. Appl. Biochem.* 11:581–601 (1989)), *Acinetobacter* sp. AK 226 (Yamamoto et al., *Agric. Biol. Chem.* 55:1459–1473 (1991)), *Alcaligenes faecalis* ATCC 8750 (Yamamoto et al., *J. Ferment. Bioeng.* 73:425–430 (1992)), and *Acidovorax facilis* 72W (Gavagan et al., *J. Org. Chem.* 63:4792–4801 (1998)).

The gene encoding the *A. facilis* 72W (ATCC 55746) nitrilase has been cloned and recombinantly expressed (WO 01/75077) and Chauhan et al., *Appl Microbiol Biotechnol,* 61:118–122 (2003)). The *A. facilis* 72W nitrilase converts 3-hydroxynitriles to the corresponding 3-hydroxycarboxylic acids in high yield (U.S. Pat. No. 6,562,603). The 3-hydroxyacids produced are useful as substrates for the preparation of polymers including highly branched copolyesters. Two particularly useful 3-hydroxycarboxylic acids are 3-hydroxyvaleric acid (3-HVA) and 3-hydroxybutyric acid (3-HBA). Nitrilases having improved nitrilase activity for the conversion of 3-hydroxyvaleronitrile (3-HVN) or 3-hydroxybutyronitrile (3-HBN) to the corresponding 3-hydroxycarboxylic acid in high yield at up to 100% conversion would be very useful for reducing industrial production costs.

The problem to be solved, therefore, is to provide nitrilase enzymes with activity useful for converting 3-hydroxynitriles to their corresponding carboxylic acids in high yield. More specifically, nitrilase enzymes possessing a significant improvement in nitrilase activity (relative to the nitrilase activity of the *A. facilis* 72W) for the conversion of 3-hydroxynitriles (e.g., 3-hydroxyvaleronitrile or 3-hydroxybutyronitrile) to the respective 3-hydroxycarboxylic acids would be useful for reducing industrial production costs.

SUMMARY OF THE INVENTION

An embodiment of the invention is an isolated nucleic acid fragment encoding an enzymatically-active nitrilase polypeptide, the polypeptide having a polypeptide sequence selected from the group consisting of SEQ ID NO:6, 8, 12, 14, 16, and 18 and having nitrilase activity at least 1.8-fold higher in comparison to the nitrilase activity of the *A. facilis* 72W (ATCC 55746) nitrilase when converting 3-hydroxyvaleronitrile to 3-hydroxyvaleric acid under identical reaction conditions.

The invention is also embodied in an isolated nucleic acid fragment, the nucleic acid fragment selected from the group consisting of SEQ ID NOs:5, 7, 11, 13, 15, and 17, wherein isolated the nucleic acid fragment encodes a polypeptide having an improvement in nitrilase activity at least 1.8-fold higher relative to the activity of *A. facilis* 72W (ATCC 55746) nitrilase when converting 3-hydroxyvaleronitrile to 3-hydroxyvaleric acid under identical aqueous reaction conditions. Additional embodiments of the invention include a polypeptide encoded by the nucleic acid fragments of the invention; a chimeric gene comprising the isolated nucleic acid fragment of the invention operably linked to a suitable regulatory sequence; an expression cassette comprising the chimeric gene of the invention; a transformed microorganism comprising the chimeric gene of the invention; and a transformed microorganism comprising the expression cassette of the invention.

A further embodiment is an improved process for hydrolyzing a 3-hydroxynitrile to a 3-hydroxycarboxylic acid comprising the steps of: (a) contacting a 3-hydroxynitrile in an aqueous reaction mixture with an improved nitrilase catalyst characterized by at least a 1.8-fold improvement in nitrilase activity in comparison to the activity of the *A. facilis* 72W (ATCC 55746) nitrilase under identical reaction conditions, the improved nitrilase catalyst encoded by the isolated nucleic acid fragment of the invention; and (b) recovering the 3-hydroxycarboxylic acid produced in step (a).

A further embodiment of the invention is an improved process for hydrolyzing 3-hydroxyvaleronitrile to 3-hydroxyvaleric acid comprising the steps of: (a) contacting 3-hydroxyvaleronitrile in an aqueous reaction mixture with a nitrilase catalyst encoded by the isolated nucleic acid fragment of the invention characterized by at least a 1.8-fold improvement in nitrilase activity relative to the activity of the *A. facilis* 72W (ATCC 55746) nitrilase under identical reaction conditions; and (b) recovering the 3-hydroxyvaleric acid produced in step (a).

A further embodiment of the invention is an improved process for hydrolyzing 3-hydroxybutyronitrile to 3-hydroxybutyric acid comprising the steps of: (a) contacting 3-hydroxybutyronitrile in an aqueous reaction mixture with an enzymatically active nitrilase catalyst having the polypeptide sequence of SEQ ID NO:6 and characterized by at least a 1.9-fold improvement in nitrilase activity relative to the activity of the *A. facilis* 72W (ATCC 55746) nitrilase under identical reaction conditions; and (b) recovering the 3-hydroxybutyric acid produced in step (a).

BRIEF DESCRIPTION OF THE SEQUENCES PROVIDED

The invention can be more fully understood from the following detailed description and the accompanying computer readable form of a Sequence Listing, the content of which is incorporated by reference as a part of this application.

The following sequences are in conformity with 37 C.F.R. 1.821–1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleic acid sequence of a primer used for error-prone PCR and for amplifying the *A. facilis* 72W nitrilase.

SEQ ID NO:2 is the nucleic acid sequence of a primer used for error-prone PCR and for amplifying the *A. facilis* 72W nitrilase.

SEQ ID NO:3 is the nucleic acid sequence of the *A. facilis* 72W nitrilase coding sequence used as a control in plasmid pNM18. The sequence is identical to the wild-type *A. facilis* 72W nitrilase sequence except for a change in the start codon from GTG to ATG in order to facilitate expression in *E. coli*.

SEQ ID NO:4 is the deduced amino acid sequence for the *A. facilis* 72W nitrilase expressed from plasmid pNM18.

SEQ ID NO:5 is the nucleic acid sequence of the mutant nitrilase coding sequence found in plasmid pNM18/B2 and pNM18/H9.

SEQ ID NO:6 is the deduced amino acid sequence of the mutant nitrilase expressed from plasmid pNM18/B2 and pNM18/H9.

SEQ ID NO:7 is the nucleic acid sequence of the mutant nitrilase coding sequence found in plasmid pNM18/B4.

SEQ ID NO:8 is the deduced amino acid sequence of the mutant nitrilase expressed from plasmid pNM18/B4.

SEQ ID NO:9 is the nucleic acid sequence of a primer used for creating a mutant nitrilase having a single amino acid substitution at residue position 210 of the *A. facilis* 72W nitrilase (Thr210→Met).

SEQ ID NO:10 is the nucleic acid sequence of a primer used for creating a mutant nitrilase having a single amino acid substitution at residue position 210 of the *A. facilis* 72W nitrilase (Thr210→Met).

SEQ ID NO:11 is the nucleic acid sequence of the mutant nitrilase containing a codon change which resulted in a single amino acid substitution at residue position 210 (Thr210→Cys) of the *A. facilis* 72W nitrilase.

SEQ ID NO:12 is the deduced amino acid sequence of the mutant nitrilase containing a single amino acid substitution at residue position 210 (Thr210→Cys) of the *A. facilis* 72W nitrilase.

SEQ ID NO:13 is the nucleic acid sequence of the mutant nitrilase containing a codon change which resulted in a single amino acid substitution at residue position 168 (Phe168→Lys) of the *A. facilis* 72W nitrilase.

SEQ ID NO:14 is the deduced amino acid sequence of the mutant nitrilase containing a single amino acid substitution at residue position 168 (Phe168→Lys) of the *A. facilis* 72W nitrilase.

SEQ ID NO:15 is the nucleic acid sequence of the mutant nitrilase containing a codon change which resulted in a single amino acid substitution at residue position 168 (Phe168→Val) of the *A. facilis* 72W nitrilase.

SEQ ID NO:16 is the deduced amino acid sequence of the mutant nitrilase containing a single amino acid substitution at residue position 168 (Phe168→Val) of the *A. facilis* 72W nitrilase.

SEQ ID NO:17 is the nucleic acid sequence of the mutant nitrilase containing a codon change which resulted in a single amino acid substitution at residue position 168 (Phe168→Leu) of the *A. facilis* 72W nitrilase.

SEQ ID NO:18 is the deduced amino acid sequence of the mutant nitrilase containing a single amino acid substitution at residue position 168 (Phe168→Leu) of the *A. facilis* 72W nitrilase.

BRIEF DESCRIPTION OF THE BIOLOGICAL DEPOSITS

Applicants have made the following biological deposits under the terms of the Budapest Treaty:

| Depositor Identification Reference | Int'l. Depository Designation No. | Date of Deposit |
|---|---|---|
| *Acidovorax facilis* 72W | ATCC 55746 | 8 Mar. 1996 |
| *E. coli* SS1001 | ATCC PTA-1177 | 11 Jan. 2000 |

As used herein, "ATCC" refers to the American Type Culture Collection international depository located at 10801 University Boulevard, Manassas, Va. 20110-2209 U.S.A. The "Int'l Depository Designation No." is the accession number to cultures on deposit with the ATCC.

The listed deposits will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

Several nitrilase enzymes are provided significantly improved in nitrilase activity relative to the activity of the *A. facilis* 72W (ATCC 55746) nitrilase when converting 3-hydroxynitriles to 3-hydroxycarboxylic acids in high yield at up to 100% conversion. Methods for producing 3-hydroxycarboxylic acids (3-HVA and 3-HBA) using the present nitrilases are also provided.

The *A. facilis* 72W nitrilase was mutated by error-prone PCR and/or site-directed mutagenesis to create a series of mutant nitrilases exhibiting improved nitrilase activity for converting 3-hydroxynitriles to the respective 3-hydroxycarboxylic acids. Improvements in nitrilase activity for 3-hydroxycarboxylic acid production were measured using transformed microbial host cells (unimmobilized and immobilized), as described in the accompanying Examples.

Nitrilase enzymes having the ability to convert the nitrile functional group of a 3-hydroxynitrile to its corresponding carboxylic acid offer significant advantages. Hydrolysis of nitriles using the present nitrilases is useful for the synthesis of 3-hydroxyacids in high yield from relatively inexpensive and readily available starting materials with very little byproduct and waste production in comparison to chemical or other enzymatic methods.

The claimed process for preparing 3-hydroxyvaleric acid or 3-hydroxybutyric acid generates little waste or reaction byproducts, and the 3-hydroxycarboxylic acid is readily recovered from the product mixture. Previously known chemical methods for the hydrolysis of 3-hydroxynitriles to 3-hydroxycarboxylic acids cannot produce the high yields and selectivities obtained using enzyme-catalyzed nitrile hydrolysis. Non-enzymatic nitrile hydrolysis reactions typically involve heating solutions of the nitrile at elevated temperatures, often times in the presence of strong acid or base, while enzyme-catalyzed reactions are carried out at ambient temperature in aqueous solution and at neutral pH with no added acid or base. For example, aqueous barium hydroxide has been used to hydrolyze 3-aminopropionitrile to 3-alanine in 85 to 90% yield (Ford, J. H., *Org. Synth.*, Coll. vol. III: 34–36 (1955)), and 3-cyanobutyric acid to methylsuccinic acid in 72% yield (Brown, G. B., *Org Synth.* Coll. vol. III: 615–617 (1955)); repeating the first of these two procedures with 3-hydroxyvaleronitrile produced little or no detectable 3-hydroxyvaleric acid (see Comparative Example).

The 3-hydroxyvaleric acid and 3-hydroxybutyric acid produced by the present invention are useful as ingredients to prepare polyesters (especially highly branched polyesters in combination with a hyperbranching hydroxycarboxylic (co)monomer) and are useful as (co)monomers in biodegradable polyester production (U.S. Pat. No. 6,562,603). Several classes of highly branched copolyester polyols have been prepared using dimethylolpropionic acid as a branching comonomer and a variety of linear hydroxycarboxylic acids and lactones. Some of these polymers demonstrate attractive characteristics. The corresponding block copolymers with similar overall composition (but of different microstructure) have been reported (e.g., DMPA/ε-caprolactone block copolymers described in Trollsåas et al., *Macromolecules,* 30:8508 (1997) and Trollsås et al., *J. Polym. Sci. Part (A): Polymer Chemistry* 36: 2793 (1998)). Highly-branched copolyester polyol substrates for reactive coatings with desirable, significantly enhanced $T_g$ have been reported when a 3-hydroxycarboxylic acid, such as 3-hydroxyvaleric acid, was substituted for E-caprolactone as a linear comonomer in the copolymerization with dimethylolpropionic acid or trimethylolacetic acid (U.S. Pat. No. 6,562,603). The higher $T_g$ significantly expands the range of applications to which branched copolyesters can be applied.

In this disclosure, a number of terms and abbreviations are used. The following definitions are provided.

A saturated "hydrocarbyl radical" is defined as any radical composed exclusively of carbon and hydrogen, where single bonds are exclusively used to join carbon atoms together. Thus, any stable arrangement of carbon and hydrogen atoms, having at least one carbon atom, is included within the scope of a saturated hydrocarbyl radical.

The terms "hyperbranched", "highly branched", and "dendritic macromolecules" (dendrimers) can generally be described as three-dimensional, highly branched molecules having a tree-like structure. Dendrimers are highly symmetrical, while similar macromolecules designated as hyperbranched or highly branched may to a certain degree hold an asymmetry, yet maintain the highly branched tree-like structure. Dendrimers can be said to be monodispersed variations of hyperbranched macromolecules. Hyperbranched, highly branched, and dendritic macromolecules normally consist of an initiator or nucleus having one or more reactive sites and a number of surrounding branching layers and, optionally, a layer of chain terminating molecules. The layers are usually called generations.

"Nitrilase catalyst" refers herein to an enzyme catalyst that is characterized by nitrilase activity. The enzyme catalyst may be in the form of a whole microbial cell, permeabilized microbial cell(s), one or more cell components of a microbial cell extract, partially purified enzyme, or purified enzyme. The terms "improved nitrilase", "mutant nitrilase", and "protein engineered nitrilase" will be used interchangeably to refer to the present nitrilases having significantly improved nitrilase activity towards the conversion of 3-hydroxynitriles (e.g. 3-hydroxyvaleronitrile or 3-hydroxybutyronitrile) to the respective 3-hydroxycarboxylic acids in comparison to the nitrilase activity of the *A. facilis* 72W nitrilase under similar reaction conditions. The *A. facilis* 72W nitrilase is represented by SEQ ID NO:3. It is identical to the wild-type *A. facilis* 72W nitrilase except for a change in the start codon from GTG to ATG (introduced to facilitate expression in *E. coli*). In the present invention, the coding sequence for the *A. facilis* 72W nitrilase (SEQ ID NO:3) expressed from pNM18 is considered to be an appropriate control for nitrilase activity comparisons.

In the present invention, "one unit of enzyme activity" or "one unit of activity" or "U" is defined as the amount of enzyme activity required for the production of 1 μmol of the specified 3-hydroxycarboxylic acid product per minute at a specified temperature. In the present invention, the exemplified 3-hydroxycarboxlic acids produced are 3-hydroxyvaleric acid and 3-hydroxybutyric acid.

In the present invention, the term "nitrilase activity" refers to the enzyme activity per unit mass (for example, milligram) of protein, dry cell weight, or bead weight. Comparisons in nitrilase activity were measured proportional to the dry cell weight or bead weight. Since nitrilase expression levels between the *A. facilis* 72W control and the improved mutants were indistinguishable as quantified using laser densitometry analysis of an SDS-PAGE gel, comparisons and reported improvements in nitrilase activity were measured relative to dry cell weight or bead weight.

The term "relative nitrilase activity" refers to the nitrilase activity expressed as a multiple (or fraction) of a reference (control) nitrilase activity. In the present invention, a "significant improvement" in relative nitrilase activity is an improvement of at least 1.2-fold higher nitrilase activity in comparison to the nitrilase activity of the control under identical reaction conditions. In another embodiment, the improvement is at least 1.8-fold higher nitrilase activity in comparison to the nitrilase activity of the control under identical reaction conditions. In a further embodiment, the improvement is at least 5-fold higher nitrilase activity in comparison to the nitrilase activity of the control under identical reaction conditions.

"3-Hydroxynitrile" is equivalent to "β-hydroxynitrile". "3-Hydroxynitriles include, but are not limited to, the following compounds: 3-hydroxypropionitrile, 3-hydroxybutyronitrile, 3-hydroxyvaleronitrile, 3-hydroxyhexanenitrile, 3-hydroxyheptanenitrile, 3-hydroxynonanenitrile, 3-hydroxy-3-isopropyl-4-methylpentanenitrile, 3-hydroxy-3-phenylpropanenitrile, 2-propyl-3-hydroxypentanenitrile and 3-hydroxy-3-methyl-n-pentanenitrile. The 3-hydroxynitriles preferred in the present invention include 3-hydroxyvaleronitrile and 3-hydroxybutyronitrile.

"3-Hydroxycarboxylic acid" is equivalent to "β-hydroxycarboxylic acid". "3-Hydroxycarboxylic acids include, but are not limited to, the following compounds: 3-hydroxypropionic acid, 3-hydroxybutyric acid, 3-hydroxypentanoic acid, 3-hydroxyhexanoic acid, 3-hydroxy-3-isopropyl-4-methylpentanoic acid, 3-hydroxy-3-phenylpropanoic acid, 2-propyl-3-hydroxypentanoic acid, 3-hydroxy-2,2-dimethylpropionic acid, and 3-hydroxy-3-methyl-n-valeric acid. 3-Hydroxycarboxylic acids produced in the present invention include 3-hydroxyvaleric acid and 3-hydroxybutyric acid. The 3-hydroxycarboxylic acid produced may be in the form of the acid or its corresponding ammonium salt.

"3-Hydroxyvaleronitrile" is also known as 3-hydroxypentanenitrile and 3-HVN.

"3-Hydroxyvaleric acid" is also known as 3-hydroxypentanoic acid and 3-HVA.

"3-Hydroxybutyronitrile" is also known as 3-hydroxybutanenitrile and 3-HBN.

"3-Hydroxybutyric acid" is also known as 3-hydroxybutanoic acid and 3-HBA.

The terms "host cell", "heterologous host cell", and "host organism" refer to a cell capable of receiving foreign or heterologous genes, gene fragments, or DNA fragments.

The terms "recombinant organism", "transformed host", "transformant", "transgenic organism", and "transformed microbial host" refer to a host organism having been transformed with heterologous or foreign DNA. The recombinant organisms of the present invention express foreign coding sequences or genes that encode active nitrilase enzyme. "Transformation" refers to the transfer of a DNA fragment into the host organism. The transferred DNA fragment can be chromosomally or extrachromosomally incorporated (i.e., via a vector) into the host organism. "Transformation cassette" refers to a specific fragment of DNA containing a set of genetic elements conveniently arranged for insertion into a host cell, usually as part of a plasmid. "Expression cassette" refers to a specific fragment of DNA containing a set of genetic elements conveniently arranged for insertion into a host cell, usually as part of a plasmid, that also allows for enhanced gene expression in the host.

The terms "plasmid" and "vector" refer to an extra chromosomal element often carrying genes which are not part of the central metabolism of the host cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction.

"Gene" refers to a nucleic acid fragment that expresses a specific protein, including regulatory sequences preceding (5' non-coding sequences) and following (3' non-coding sequences) the coding sequence. "Native gene" refers to a gene with its own regulatory sequences in an arrangement as found in nature. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of the native organism. A "foreign gene" or "heterologous gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "nucleic acid" refers to complex compounds of high molecular weight occurring in living cells, the fundamental units of that are nucleotides linked together with phosphate bridges. Nucleic acids are subdivided into two types: ribonucleic acid (RNA) and deoxyribonucleic acid (DNA).

The letters "A", "G", "T", and "C" when referred to in the context of nucleic acids, mean the purine bases (Adenine ($C_5H_5N_5$) and Guanine ($C_5H_5N_5O$)) and the pyrimidine bases (Thymine ($C_5H_6N_2O_2$) and Cytosine ($C_4H_5N_3O$)), respectively.

The terms "coding sequence" or "coding region" refers to a DNA sequence that codes for a specific amino acid sequence. The terms "ORF" and "open reading frame" and "coding sequence" and "coding region" are used interchangeably to refer to a portion of DNA sequence that translates into a protein. ORFs are usually delineated in the sequence by three base pairs designating the start (a start codon) and three base pairs designating the stop (a stop codon) in the translation of the DNA sequence into the protein sequence.

The terms "nucleic acid fragment" or "nucleotide fragment" refer to a fragment of DNA that may encode a gene and/or regulatory sequences preceding (5', upstream) or following (3', downstream) the coding sequence. A "fragment" constitutes a fraction of the complete nucleic acid sequence of a particular region. A fragment may constitute an entire gene.

The terms "restriction endonuclease" and "restriction enzyme" refer to an enzyme which catalyzes hydrolytic cleavage within a specific nucleotide sequence in double-stranded DNA.

The term "oligonucleotide" refers to primers, probes, oligomer fragments to be detected, labeled-replication blocking probes, and oligomer controls, and refers generically to polydeoxyribonucleotides (containing 2-deoxy-D-ribose), to polyribonucleotides (containing D-ribose) and to any polynucleotide which is an N-glycoside of a purine or pyrimidine base (nucleotide), or modified purine or pyrimidine base. Also included in the definition of "oligonucleotide" are nucleic acid analogs (e.g., peptide nucleic acids) and those that have been structurally modified (e.g., phosphorothioate linkages) (See also Thuong et al., *Biochimie* (1985) July-August 67(7–8):673–684.) There is no intended distinction between the length of a "nucleic acid", "polynucleotide", or an "oligonucleotide".

The term "primer" refers to an oligonucleotide (synthetic or occurring naturally), which acts as a point of initiation of nucleic acid synthesis or replication along a complementary strand when placed under conditions in which synthesis of a complementary strand is catalyzed by a polymerase.

"Suitable regulatory sequences" refer to nucleotide sequences which influence the transcription, RNA processing, RNA stability, or translation of the associated coding sequence and which are located upstream (5' non-coding sequences), within, or downstream (3' non-coding sequences) of a coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters that cause a gene to be expressed in most cell types at most times or under most environmental conditions are commonly referred to as "constitutive promoters". Promoters that cause a gene to be expressed only in the presence of a particular compound or environmental condition are commonly referred to as "inducible promoters". Since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The "3' non-coding sequences" refer to DNA sequences located downstream of a coding sequence and include polyadenylation recognition sequences (normally limited to eukaryotes) and other sequences encoding regulatory signals capable of affecting mRNA processing or gene expression. The polyadenylation signal (normally limited to eukaryotes) is usually characterized by affecting the addition of polyadenylic acid tracts to the 3' end of the mRNA precursor.

The skilled artisan is well aware of the "codon-bias" exhibited by a specific host cell in using nucleotide codons to specify a given amino acid. Therefore, when synthesizing a gene for improved expression in a host cell, it is desirable to design the gene such that its codon usage reflects the preferred codon bias of the host cell. A survey of genes derived from the host cell where sequence information is available can determine its codon bias. Codon-optimization is well known in the art and has been described for various systems including, but not limited to, yeast (Outchkourov et al., *Protein Expr Purif*, 24(1):18–24 (2002)) and *E. coli* (Feng et al., *Biochemistry*, 39(50):15399–15409 (2000)).

The term "expression" means the transcription and translation to gene product from a gene coding for the sequence of the gene product, usually a protein.

The terms "protein", "polypeptide", and "peptide" are used interchangeably to refer to the gene product expressed.

"Codon degeneracy" refers to the divergence in the genetic code permitting variation of the nucleotide sequence without affecting the amino acid sequence of an encoded polypeptide. For example, it is well known in the art that the triplet codons CTT, CTC, CTA, and CTG all code for the amino acid leucine. It is also well known in the art that alterations in a gene that produce a chemically-equivalent amino acid at a given site ("conservative changes"), but do not affect the functional properties of the encoded protein, are common. Thus, a codon for the amino acid alanine, a hydrophobic amino acid, may be substituted by a codon encoding another less hydrophobic residue (such as glycine) or a more hydrophobic residue (such as valine, leucine, or isoleucine) without affecting the functional properties of the encoded protein. Similarly, substitution of one negatively charged residue for another (such as aspartic acid for glutamic acid) or one positively charged residue for another (such as lysine for arginine) can also be expected to produce a functionally equivalent product. Nucleotide changes that result in alteration of the N-terminal and C-terminal portions of the protein molecule would also not be expected to alter the activity of the protein. Each of the proposed modifications is well within the routine skill in the art, as is determining if the biological activity of the encoded products is retained.

*Acidovorax facilis* 72W (ATCC 55746) Nitrilase

The *A. facilis* 72W nitrilase (EC 3.5.5.1) is a robust catalyst for producing carboxylic acids from aliphatic or aromatic nitriles (WO 01/75077, and Chauhan et al., (supra)). It has also been shown to catalyze the conversion of 3-hydroxynitriles to 3-hydroxycarboxylic acids (U.S. Pat. No. 6,562,603).

All known nitrilases, including *A. facilis* 72W nitrilase, have a nucleophilic cysteine in the enzyme active site (Cowan et al., *Extremophiles*, 2:207–216 (1998); Pace, H. and Brenner, C., *Genome Biology*, 2(1):reviews 1–9 (2001); and Chauhan et al., supra) and all are susceptible to inactivation by thiol reagents (1.0 mM concentrations of copper chloride, silver nitrate, mercuric acetate, or ferric chloride each produced major decreases in *A. facilis* 72W nitrilase enzyme activity). Cysteine residues are also capable of being irreversibly oxidized to sulfinic acids, resulting in a loss of enzyme activity. Despite the sensitivity of nitrilase enzymes to various inactivating mechanisms, immobilized *A. facilis* 72W cells are robust, retaining much of their nitrilase activity after numerous recycle reactions (WO 01/75077).

Sequence comparisons of the *A. facilis* 72W nitrilase to other bacterial nitrilases has been reported (Chauhan et al., supra). The 72W nitrilase has several conserved signature domains including a 16-amino acid region near the amino terminus (amino acid residues 40–55 of SEQ ID NO:4) and the catalytic region (amino acid residues 160–173 of SEQ ID NO:4) containing the essential cysteine residue. This cysteine residue (Cys164 of SEQ ID NO:4), along with conserved glutamic acid (Glu48 of SEQ ID NO:4) and lysine residues (Lys130 of SEQ ID NO:4), form the catalytic triad motif found in all nitrilases (Pace, H., and Brenner, C., supra). Despite some structural similarities conserved among the reported nitrilases, substrate specificity of the enzymes varies widely (O'Reilly, C. and Turner, P., *J Appl Microbiol*, 95:1161–1174 (2003)).

Enzyme Properties

Mutant 72W nitrilases having improved relative nitrilase activity towards the conversion of 3-hydroxyvaleronitrile to 3-hydroxyvaleric acid or 3-hydroxybutyronitrile to 3-hydroxybutyric acid were assayed under the specified conditions. Screening methods measuring 3-HVN to 3-HVA conversion were used to select those nitrilase mutants having improved nitrilase activity.

Improvements in nitrilase activity were determined by comparison to the nitrilase activity of the control (*A. facilis* 72W (ATCC 55746) nitrilase). Nitrilase activity was calculated by dividing the measured units of activity (U) by catalyst weight. The catalyst weight can be measured in terms of purified protein weight, wet cell weight, dry cell weight or weight of the immobilized catalyst (i.e., GA/PEI-crosslinked catalyst/alginate beads). In the present invention, the nitrilase activity was reported as units of activity per gram of dry cell weight (U/g DCW) or units of activity per gram of catalyst bead (immobilized catalyst comparisons). With nitrilase activity comparisons based on dry cell weight as the unit catalyst weight, the level of nitrilase protein production must be considered. The expression levels between the various transformants and the control were measured and observed to be essentially identical. Thus, improvements in the reported nitrilase activity for the various mutants were attributed to structural modifications to the enzyme.

The coding sequences of the present mutant nitrilases (and also of the *A. facilis* 72W (ATCC 55746) nitrilase control) were expressed in identical vector (pTrcHis2-TOPO) and host (*E. coli* TOP10) or *E. coli* FM5 backgrounds. SDS-PAGE analyses (as quantified using laser densitometry) demonstrated that nitrilase protein expression levels in each mutant (and control) were essentially equal (as expected due to the identical expression system and host used). The relative enzyme activity was reported as the fold increase in nitrilase activity measured for the various mutant catalysts relative to the nitrilase activity measured in the *E. coli* control transformant (pNM18) expressing the *A. facilis* 72W nitrilase.

For unimmobilized catalysts, nitrilase activity of the mutant nitrilases (U/g dry cell weight) was determined by measuring the rate of conversion of a 0.5 M solution of 3-hydroxynitrile to 3-hydroxycarboxylic acid at 25° C. (pH 7.0) per gram of dry cell weight. For immobilized catalyst comparisons, specific activity was determined by measuring the rate of conversion of a 0.4 M solution of 3-HVN to 3-HVA at 35° C. (pH 7.0) and reported as units of nitrilase activity per gram of bead (U/g bead). One unit of nitrilase activity (U) is equivalent to production of 1 micromole 3-hydroxycarboxylic acid/min at 25° C. (or 35° C. for immobilized catalyst). In the present invention, units of nitrilase activity are reported based on the production of 3-hydroxyvaleric acid or 3-hydroxybutyric acid.

For a particular mutant nitrilase, point substitution mutations within the DNA coding region and the resulting amino acid change are specified with reference to the *Acidovorax facilis* 72W amino acid sequence (SEQ ID NO:4), using one of the following formats:

1. Extended format: the wild-type amino acid is provided (using the standard 3-letter abbreviation) along with the corresponding amino acid residue position within SEQ ID NO:4 followed by the new amino acid found within the mutant at the same residue position. For example, "Thr210 to Ala" or "Thr210→Ala" describes a mutation in the SEQ ID NO:4 at amino acid residue position 210 where threonine was changed to alanine as a result of the mutation.

2. Short-hand format: the wild-type amino acid (denoted by the standard single letter abbreviation) is followed by the amino acid residue position of SEQ ID NO:4 followed by the mutant amino acid (also denoted by the standard single letter abbreviation). For example, "T210A" describes a mutation in SEQ ID NO:4 at amino acid residue position 210 where threonine was changed to alanine as a result of the mutation.

Hydrolysis of 3-Hydroxynitrile to 3-Hydroxycarboxylic Acid:

The hydrolysis reaction was performed by mixing a 3-hydroxynitrile (for example, 3-hydroxyvaleronitrile or 3-hydroxybutyronitrile) with an aqueous suspension of the enzyme catalyst. Whole recombinant microbial cells (expressing the present mutant nitrilases) can be used as an enzyme catalyst without any pretreatment. Alternatively, the microbial cells can be immobilized in a polymer matrix (e.g., alginate beads or polyacrylamide gel (PAG) particles) or on an insoluble solid support (e.g., celite) to facilitate recovery and reuse of the enzyme catalyst. Purified or partially-purified enzyme(s) can also be isolated from the whole cells and used directly as a catalyst, or the enzyme(s) can be immobilized in a polymer matrix or on an insoluble support. The immobilization of the *A. facilis* 72W nitrilase has previously been reported (WO 01/75077). Methods for the immobilization of cells or for the isolated enzymes have been widely reported and are well known to those skilled in the art (Methods in Biotechnology, Vol. 1: *Immobilization of Enzymes and Cells*; Gordon F. Bickerstaff, Editor; Humana Press, Totowa, N.J., USA; 1997).

The concentration of enzyme catalyst in the aqueous reaction mixture depends on the specific catalytic activity of the enzyme catalyst and is chosen to obtain the desired rate of reaction. The wet cell weight of the microbial cells used as catalyst in hydrolysis reactions typically ranges from 0.001 grams to 0.250 grams of wet cells per mL of total reaction volume, preferably from 0.002 grams to 0.050 grams of wet cells per mL.

The temperature of the hydrolysis reaction is chosen to optimize both the reaction rate and the stability of the enzyme catalyst activity. The temperature of the reaction may range from just above the freezing point of the reaction mixture (approximately 0° C.) to 65° C., with a preferred range of reaction temperature of from 5° C. to 35° C. The microbial cell catalyst suspension may be prepared by suspending the cells in distilled water, or in a aqueous solution of a buffer which will maintain the initial pH of the reaction between 5.0 and 10.0, preferably between 6.0 and 9.0. As the reaction proceeds, the pH of the reaction mixture may change due to the formation of an ammonium salt of the carboxylic acid from the corresponding nitrile functionality. The reaction can be run to complete conversion of 3-hydroxyvaleronitrile or 3-hydroxybutyronitrile with no pH control, or a suitable acid or base can be added over the course of the reaction to maintain the desired pH.

3-Hydroxyvaleronitrile and 3-hydroxybutyronitrile were found to be completely miscible with water in all proportions at 25° C. In cases where reaction conditions are chosen such that the solubility of the 3-hydroxynitrile is also dependent on the temperature of the solution and/or the salt concentration (buffer or product 3-hydroxycarboxylic acid ammonium salt) in the aqueous phase, the reaction mixture may initially be composed of two phases: an aqueous phase containing the enzyme catalyst and dissolved 3-hydroxynitrile, and an organic phase (the undissolved 3-hydroxynitrile). As the reaction progresses, the 3-hydroxynitrile dissolves into the aqueous phase, and eventually a single phase product mixture is obtained. The reaction may also be run by adding the 3-hydroxynitrile to the reaction mixture at a rate approximately equal to the enzymatic hydrolysis reaction rate, thereby maintaining a single-phase aqueous reaction mixture, and avoiding the potential problem of substrate inhibition of the enzyme at high starting material concentrations.

3-Hydroxyvaleric acid or 3-hydroxybutyric acid may exist in the product mixture as a mixture of the protonated carboxylic acid and its corresponding ammonium salt (dependent on the pH of the product mixture), and may additionally be present as a salt of the carboxylic acid with any buffer that may additionally be present in the product mixture. The 3-hydroxycarboxylic acid product may be isolated from the reaction mixture as the protonated carboxylic acid, or as a salt of the carboxylic acid, as desired.

The final concentration of 3-hydroxycarboxylic acid in the product mixture at complete conversion of 3-hydroxynitrile may range from 0.001 M to the solubility limit of the 3-hydroxycarboxylic acid product. Preferably, the concentration of 3-hydroxyvaleric acid will range from 0.10 M to 2.0 M. 3-Hydroxyvaleric acid may be isolated from the product mixture (after removal of the catalyst) by adjusting the pH of the reaction mixture to between 1.0 and 2.5 with concentrated hydrochloric acid, saturation of the resulting solution with sodium chloride, and extraction of 3-hydroxyvaleric acid with a suitable organic solvent such as methyl t-butyl ether, ethyl ether, or dichloromethane. The combined organic extracts are then combined, stirred with a suitable drying agent (e.g., magnesium sulfate), filtered, and the solvent removed (e.g., by rotary evaporation) to produce the desired product in high yield and in high purity (typically 98–99% pure). If desired, the product can be further purified by recrystallization or distillation.

The enzymatic hydrolysis of 3-hydroxybutyronitrile to 3-hydroxybutyric acid was performed using methods similar to those described above for 3-hydroxyvaleronitrile (see accompanying Examples), and produced 3-hydroxybutyric acid in 100% yield at up to 100% conversion of 3-hydroxybutyronitrile.

Polymer Synthesis Using 3-Hydroxycarboxylic Acids

Synthesis of highly-branched copolyesters using linear a 3-hydrocarboxylic acid or its ester has previously been reported (U.S. Pat. No. 6,562,603), wherein at least two repeat units are derived from at least one linear 3-hydroxycarboxylic acid or its ester of the structure $R^1O—CR^4R^5CR^6R^7C(O)OR^1$ and at least one hyperbranching hydroxycarboxylic acid or its ester of the structure $(R^2O)_n—R—[C(O)OR^1]_m$, wherein R is $C_{1-12}$ hydrocarbyl radical or a partially or completely substituted hydrocarbyl radical with n+m free valencies, where some or all hydrogen atoms may be substituted with carbon atoms, $R^1$ is H, $C_{1-12}$ or hydroxyl substituted $C_{1-12}$ hydrocarbyl radical, $R^3$, $R^4$, $R^5$, $R^6$, $R^7$ is H or $C_{1-12}$ hydrocarbyl radical, $R^2$ is H or $(O)CR^3$, n+m is 3 or more, and provided that one of n and m is 1, these repeat units may also be derived from equivalent compounds that will form polyesters, such as esters of the hydroxycarboxylic acids. The compound $(R^2O)_n—R—[C(O)OR^1]_m$, by virtue of being a tri- or higher functional, is sometimes called a hyperbranching monomer. More than one such monomer may be present in such a polymerization. It is preferred that n+m is three or four. Normal esterification catalysts well known in the art may be used with these monomers to form polyesters (for example, a protonic acid, Lewis acid, or a basic catalyst including sulfonic acids, phosphoric and phosphonic acids, titanium alkoxides, dialkyltin oxide, oxides, carbonates and carboxylates of tin, zinc, manganese, calcium, magnesium, or antimony). Methods for making polyesters are well known in the art.

Analysis of 3-Hydroxycarboxylic Acids

Analytical methods suitable for analyzing the production of 3-hydroxycarboxylic acids are well known in the art including, but not limited to, HPLC, CE, GC, and MS. For example, HPLC analysis was used to determine the amount of 3-hydroxyvaleric acid production using a refractive index detector and either a Supelco LC-18-DB column (15 cm×4.6 mm diameter) with 7.5% (v/v) methanol in aqueous 10 mM acetic acid/10 mM sodium acetate as mobile phase (for 3-hydroxyvaleronitrile reactions), or a Bio-Rad HPX-87H column (30 cm×7.8 mm dia.) and 0.001 N sulfuric acid as mobile phase at 50° C. (for 3-hydroxybutyronitrile reactions).

Microbial Expression

The present nitrilase mutants may be produced in heterologous host cells, preferably in microbial hosts. Particularly useful in the present invention will be cells that are readily adaptable to large-scale fermentation methods. Such organisms are well known in the art of industrial bioprocessing, examples of which may be found in *Recombinant Microbes for Industrial and Agricultural Applications*, Murooka et al., eds., Marcel Dekker, Inc., New York, N.Y. (1994), and include fermentative bacteria as well as yeast and filamentous fungi. Host cells may include but are not limited to *Comamonas* sp., *Corynebacterium* sp., *Brevibacterium* sp., *Rhodococcus* sp., *Azotobacter* sp., *Citrobacter* sp., *Enterobacter* sp., *Clostridium* sp., *Klebsiella* sp., *Salmonella* sp., *Lactobacillus* sp., *Aspergillus* sp., *Saccharomyces* sp., *Zygosaccharomyces* sp., *Pichia* sp., *Kluyveromyces* sp., *Candida* sp., *Hansenula* sp., *Dunaliella* sp., *Debaryomyces* sp., *Mucor* sp., *Torulopsis* sp., *Methylobacteria* sp., *Bacillus* sp., *Escherichia* sp., *Pseudomonas* sp., *Rhizobium* sp., and *Streptomyces* sp. Particularly preferred is *E. coli*. Examples of suitable *E. coli* host cells in which a mutant nitrilase gene can be expressed include, but are not limited to, host cells specified herein and MG1655 (ATCC 47076), FM5 (ATCC 53911), W3110 (ATCC 27325), MC4100 (ATCC 35695), W1485 (ATCC 12435), and their derivatives.

Heterologous expression of the *A. facilis* 72W nitrilase has previously been reported (Chauhan et al., supra and WO 01/75077. Chauhan et al. report an *E. coli* strain (*E. coli* SS1001 (ATCC PTA-1177)) that expressed active *A. facilis* 72W nitrilase. The coding sequence of the recombinantly expressed (*E. coli* SS1001) nitrilase contained two minor sequence changes in comparison to the wild-type 72W nitrilase sequence (SEQ ID NO:3). The start codon was changed from GTG to ATG to facilitate recombinant expression and an artifact was introduced during cloning that resulted in a single amino acid change near the C-terminal (Pro367 [CCA]→Ser [TCA]).

The present mutant nitrilases, as represented by coding sequence provided by SEQ ID NOs:5, 7, 11, 13, 15, and 17, were expressed in a recombinant host (*E. coli*). Recombinant expression in an industrially-suitable host has several advantages. First, the genetic toolbox for many of the commonly used production hosts is usually well developed in comparison to the genetic tools available for many of the microorganisms from which the gene of interest was obtained. Recombinant expression in these hosts is normally more cost effective than expression in the native host. For example, it has been shown that *A. facilis* 72W cells grow on glycerol, a relatively expensive carbon substrate, when grown by fermentation, and have not been successfully grown using inexpensive glucose. In contrast, *E. coli* transformants can be grown on glucose to the same cell density as *A. facilis* 72W cells in about half the time, significantly reducing biocatalyst production costs (WO 01/75077).

Microbial expression systems and expression vectors containing regulatory sequences that direct high level expression of foreign proteins are well known to those skilled in the art. These could be used to construct chimeric genes for production of the gene products of the present mutant nitrilases. These chimeric genes could then be introduced into appropriate microorganisms via transformation to provide high level expression of the mutant nitrilase enzymes. The nucleotides of the present invention are used to produce gene products having enhanced or altered activity levels relative to that of the native *A. facilis* 72W nitrilase.

Additionally, chimeric genes will be effective in altering the properties of a host cell. For example, introducing at least one copy of chimeric genes encoding the present nitrilases under the control of the appropriate promoters into a host cell gives the host cell an improved ability to convert 3-hydroxyvaleronitrile or 3-hydroxybutyronitrile to 3-hydroxyvaleric acid or 3-hydroxybutyric acid, respectively. The chimeric genes of the instant invention will comprise suitable regulatory sequences useful for driving gene expression of the present mutant nitrilase sequences. Regulatory sequences will include, but are not limited to promoters, translation leader sequences, and ribosomal binding sites. It is preferred if these sequences are derived from the host organism; however, the skilled person will recognize that heterologous regulatory sequences may also be used.

Chimeric genes can be introduced into an appropriate host by cloning it into a suitable expression vector. Vectors or cassettes useful for the transformation of suitable host cells are well known in the art. Typically, the vector or cassette contains sequences directing transcription and translation of the relevant gene, a selectable marker, and sequences allowing autonomous replication or chromosomal integration. Suitable vectors comprise a region 5' of the coding sequence that harbors transcriptional initiation controls and a region 3' of the DNA fragment which controls transcriptional termination. It is most preferred when both control regions are derived from genes homologous to the host cell, although such control regions need not be derived from the genes native to the specific species chosen as a production host.

In one embodiment, the regulatory sequences will include a promoter. Promoters may be constitutive or inducible. Inducible promoters are generally responsive to a specific stimulus (e.g., IPTG inducing the lac promoter). Inducible promoters may be responsive to a variety of stimuli, including, chemicals, growth cycle, changes in temperature, changes in pH and changes in osmolarity, to name only a few.

Initiation control regions or promoters, which are useful to drive expression of the present mutant nitrilases in the desired host cell are numerous and familiar to those skilled in the art, including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, trp, 1$P_L$, 1$P_R$, T7, tac, $P_{BAD}$, npr, and trc (useful for expression in *Escherichia coli*). Examples include at least one of the promoters selected from the groups consisting of the tryptophan operon promoter Ptrp of *E. coli*, a lactose operon promoter Plac of *E. coli*, a Ptac promoter of *E. coli*, a phage lambda right promoter $P_R$, a phage lambda left promoter $P_L$, a T7 promoter, and a promoter of the GAP gene from *Pichia pastoris*, or is at least one strong promoter selected from the group of microorganisms consisting of *Comamonas, Corynebacterium, Brevibacterium, Rhodococcus, Azotobacter, Citrobacter, Enterobacter, Clostridium, Klebsiella, Salmonella, Lactobacillus, Aspergillus, Saccharomyces, Pichia, Zygosaccharomyces, Kluyveromyces, Candida, Hansenula, Dunaliella, Debaryomyces, Mucor, Torulopsis, Methylobacteria, Bacillus, Escherichia, Pseudomonas, Rhizobium,* and *Streptomyces*.

Termination control regions may also be derived from various genes native to the preferred hosts. Optionally, a termination site may be unnecessary; however, it is most preferred if included.

Additionally, the inserted genetic material may include a ribosome binding site. The ribosome binding site may be from a phage lambda CII gene or is selected from the group consisting of ribosome binding sites from a gene of *Comamonas, Corynebacterium, Brevibacterium, Rhodococcus, Azotobacter, Citrobacter, Enterobacter, Clostridium, Klebsiella, Salmonella, Lactobacillus, Aspergillus, Saccharomyces, Zygosaccharomyces, Pichia, Kluyveromyces, Candida, Hansenula, Dunaliella, Debaryomyces, Mucor, Torulopsis, Methylobacteria, Bacillus, Escherichia, Pseudomonas, Rhizobium,* and *Streptomyces*.

Optionally, instant gene products may preferably be a secretion product of the transformed host. Secretion of desired proteins into the growth media simplifies purification procedures and reduces costs. Secretion signal sequences are often useful in facilitating the active transport of expressible proteins across cell membranes. A transformed host capable of secretion may be created by incorporating in the host a DNA sequence that codes for a secretion signal. Methods for choosing appropriate signal sequences are well known in the art (see for example EP 546049; WO 9324631). The secretion signal DNA may be located between the expression-controlling DNA and the instant coding sequence or coding sequence fragment, and in reading frame with the latter.

Protein Engineering

The present mutant nitrilases were produced by mutagenesis. It is contemplated that the present nucleotides may be used to produce gene products having further enhanced or altered activity. Various methods are known for mutating a native gene sequence to produce a gene product with altered or enhanced activity including, but not limited to 1) random mutagenesis, 2) domain swapping (using zinc finger domains or restriction enzymes, 3) error-prone PCR (Melnikov et al., *Nucleic Acids Research*, 27(4): 1056–1062 (1999)); 4) site directed mutagenesis (Coombs et al., *Proteins* (1998), pp 259–311, 1 plate. Angeletti, Ruth Hogue, Ed., Academic: San Diego, Calif.); and 5) "gene shuffling" (U.S. Pat. No. 5,605,793; U.S. Pat. No. 5,811,238; U.S. Pat. No. 5,830,721; and U.S. Pat. No. 5,837,458, incorporated herein by reference).

The polymerase chain reaction (PCR) can be used to amplify a DNA fragment with the concomitant creation of numerous mutations by mis-incorporation of nucleotides. This can be achieved by modifying the PCR conditions such as altering the ratios of dNTPs or adding various amounts of manganese chloride in the reaction (Fromant et al., *Anal Biochem*, 224(1):347–53 (1995); Lin-Goerke et al., *Biotechniques*, 23(3):409–12 (1997)). The pool of mutated DNA fragments can then be cloned to yield a library of mutated plasmids that can then be screened following expression in a host such as *E. coli*.

The method of gene shuffling is particularly attractive due to its facile implementation, and high rate of mutagenesis and ease of screening. The process of gene shuffling involves the restriction endonuclease cleavage of a gene of interest into fragments of specific size in the presence of additional populations of DNA regions having similarity and/or difference to the gene of interest. This pool of fragments will then be denatured and reannealed to create a mutated gene. The mutated gene is then screened for altered activity.

The instant microbial sequences of the present invention may be mutated and screened for altered or enhanced activity by this method. The sequences should be double-stranded and can be of various lengths ranging from 50 bp to 10 kB. The sequences may be randomly digested into fragments ranging from about 10 bp to 1000 bp, using restriction endonuclease well known in the art (Sambrook, J., Fritsch, E. F. and Maniatis, T., *Molecular Cloning: A Laboratory Manual*, $2^{nd}$ ed., Cold Spring Harbor Laboratory: Cold Spring Harbor, N.Y. (1989); hereinafter "Maniatis"). In addition to the instant microbial sequences, populations of fragments that are hybridizable to all or portions of the microbial sequence may be added. Similarly, a population of fragments, which are not hybridizable to the instant sequence, may also be added. Typically these additional fragment populations are added in about a 10 to 20 fold excess by weight as compared to the total nucleic acid. Generally, if this process is followed, the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double-stranded nucleic acid. Preferably the temperature is from about 80° C. to 100° C. The nucleic acid fragments may be reannealed by cooling. Preferably the temperature is from about 20° C. to 75° C. Renaturation can be accelerated by the addition of polyethylene glycol ("PEG") or salt. A suitable salt concentration may range from 0 mM to 200 mM. The annealed nucleic acid fragments are then incubated in the presence of a nucleic acid polymerase and dNTPs (i.e., dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably the cycle is repeated from about 2 to 50 times, more preferably the sequence is repeated from 10 to 40 times. The resulting nucleic acid is a larger double-stranded polynucleotide ranging from about 50 bp to about 100 kB and may be screened for expression and altered activity by standard cloning and expression protocols (Maniatis, supra).

Furthermore, a hybrid protein can be assembled by fusion of functional domains using the gene shuffling (exon shuffling) method (Nixon et al., *PNAS*, 94:1069–1073 (1997)).

The functional domain of the instant gene can be combined with the functional domain of other genes to create novel enzymes with desired catalytic function. A hybrid enzyme may be constructed using PCR overlap extension methods and cloned into various expression vectors using the techniques well known to those skilled in art.

Industrial Production of 3-Hydroxycarboxylic Acids

Where commercial production of a 3-hydroxycarboxylic acid is desired using the present mutated nitrilase genes, a variety of culture methodologies may be applied for producing nitrilase catalysts. Fermentations, which may be run in the batch, fed-batch, or continuous mode, are common and well known in the art (Thomas D. Brock in *Biotechnology: A Textbook of Industrial Microbiology*, Second Edition (1989) Sinauer Associates, Inc., Sunderland, Mass., (1989); Deshpande, Mukund V., *Appl. Biochem. Biotechnol.* 36(3):227–234 (1992)).

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen, and the partial pressure of waste gases such as $CO_2$. Batch and Fed-Batch culturing methods are common and well known in the art and examples may be found in Brock (supra) and Deshpande (supra).

Commercial production of nitrilase catalysts may also be accomplished with a continuous culture. Continuous cultures are an open system where a defined culture media is added continuously to a bioreactor and an equal amount of conditioned media is removed simultaneously for processing. Continuous cultures generally maintain the cells at a constant high-liquid-phase density where cells are primarily in log phase growth. Alternatively, continuous culture may be practiced with immobilized cells where carbon and nutrients are continuously added and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end cell concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady-state growth conditions and thus the cell loss due to media being drawn off must be balanced against the cell growth rate in the culture. Methods of modulating nutrients and growth factors for continuous culture processes, as well as techniques for maximizing the rate of cell formation, are well known in the art of industrial microbiology and a variety of methods are detailed by Brock (supra).

Fermentation media in the present invention must contain suitable carbon substrates. Suitable substrates may include, but are not limited to, monosaccharides such as glucose and fructose, disaccharides such as lactose or sucrose, polysaccharides such as starch or cellulose or mixtures thereof, and unpurified mixtures from renewable feedstocks such as cheese whey permeate, cornsteep liquor, sugar beet molasses, and barley malt. Hence, it is contemplated that the source of carbon utilized in the present invention may encompass a wide variety of carbon-containing substrates and will only be limited by the choice of organism.

EXAMPLES

Materials and methods suitable for the maintenance and growth of bacterial cultures are well known in the art. Techniques suitable for use in the following examples may be found in *Manual of Methods for General Bacteriology*; Phillipp Gerhardt, R. G. E. Murray, Ralph N. Costilow, Eugene W. Nester, Willis A. Wood, Noel R. Krieg and G. Briggs Phillips, Eds.; American Society for Microbiology: Washington, D.C., (1994) or in Brock (supra).

Procedures required for PCR amplification, DNA modifications by endo- and exo-nucleases for generating desired ends for cloning of DNA, ligations, and bacterial transformation are well known in the art. Standard recombinant DNA and molecular cloning techniques used here are well known in the art and are described by Maniatis (supra); and by T. J. Silhavy et al. (in *Experiments with Gene Fusions*, (1984) Cold Spring Harbor Laboratory Press, Cold Spring, N.Y.); and by Ausubel et al. (in *Current Protocols in Molecular Biology* (1994–1998) John Wiley & Sons, Inc., New York).

All reagents, and materials used for the growth and maintenance of bacterial cells, were obtained from Aldrich Chemicals (Milwaukee, Wisc.), DIFCO Laboratories (Detroit, Mich.), GIBCO/BRL (Gaithersburg, Md.), or Sigma Chemical Company (St. Louis, Mo.) unless otherwise specified. 3-Hydroxyvaleronitrile has been prepared by reacting hydrogen cyanide with 1,2-epoxybutane in the presence of triethylaluminum (FR 1446127), and by the reaction of acetonitrile and propionaldehyde in the presence of di-n-butylboryl triflate (Hamana et al., *Chem. Lett.* 1401–1404 (1982)). Optically active 3-hydroxyvaleronitrile has been prepared by the lipase-catalyzed hydrolysis of 2-cyano-1-methylethyl acetate (Itoh et al., *J. Org. Chem.* 62:9165–9172 (1997)).

The abbreviations in the specification correspond to units of measure, techniques, properties, or compounds as follows: "s" means second(s), "min" means minute(s), "h" means hour(s), "d" means day(s), "μL" means microliter, "mL" means milliliter(s), "L" means liter(s), "mM" means millimolar, "M" means molar, "mmol" means millimole(s), "amp" means ampicillin, "kb" means kilo base(s), "kd" means kilodalton(s), "nm" means nanometer(s), and "wt" means weight, "ORF" means open reading frame, "PCR" means polymerase chain reaction, "SSC" means saline-sodium citrate buffer, "HPLC" means high performance liquid chromatography, "ca." means approximately, "rxn" means reaction, "dcw" means dry cell weight, "OD" means optical density at the designated wavelength, "AU" means absorbance units, "rpm" means revolutions per minute, "slpm" means standard liters per minute, "U" means units, "IU" means International Units, and "IPTG" means isopropyl β-D-thiogalactopyranoside.

Example 1

Construction of *A. facilis* 72W Nitrilase Random Mutagenesis Libraries by Error-prone Polymerase Chain Reaction Genomic DNA was prepared from *A. facilis* 72W (ATCC 55746) using a Puregene DNA isolation kit according to the manufacturer's instructions (Gentra Systems, Minneapolis, Minn.). Error-prone PCR was performed on the *A. facilis* 72W nitrilase gene (coding sequence; SEQ ID NO:3) using primers identified as SEQ ID NO:1 (5'-GCGCATATG GTTTCGTATAACAGCAAGTTCC-3') and SEQ ID NO:2 (5'-ATAGGATCCTTATGGCTACTTTGCTGGGACCG-3') according to instructions supplied with the GeneMorph PCR Mutagenesis Kit (Stratagene, La Jolla, Calif.). Reaction conditions recommended to produce a low mutation frequency (0–3 mutations/kb) and a medium mutation frequency (3–7 mutations/kb) were employed. Ten percent of the 1.1 kb PCR product was ligated into the expression vector pTrcHis2 TOPO according to instructions supplied with the pTrcHis2 TOPO TA Expression kit (Invitrogen, Carlsbad, Calif.). One half of the ligation mixture was transformed into *E. coli* TOP10 according to supplier's recommendations (Invitrogen). One percent of the transformation mixture was plated onto LB plates supplemented with 50 mg/L ampicillin. Resultant transformants numbered 200–400 colonies, suggesting that the total PCR product produced was capable of generating 400,000–800,000 colonies, more than enough required to screen for improved enzyme activity. Mutation frequencies were confirmed by nucleotide sequence analysis of a randomly selected sample of clones. Sequence analysis also confirmed that approximately 50% of inserts were in the forward orientation, as expected. SDS-PAGE analysis confirmed that essentially all clones with forward orientation inserts expressed the 41 kD nitrilase protein when grown and induced as recommended (Invitrogen).

In addition, the *A. facilis* 72W nitrilase gene was amplified by standard PCR using primers identified as SEQ ID NO:1 and SEQ ID NO:2, and the resulting DNA product was cloned into pTrcHis2-TOPO (Invitrogen) according to manufacturer recommendations, to generate the plasmid pNM18. Transformation of *E. coli* TOP10 with pNM18 produced a strain useful as a control. The *A. facilis* 72W nitrilase "control" sequence in pNM18 (SEQ ID NO:3) is identical to the coding sequence of the wild-type *A. facilis* 72W except for a change in the start codon from GTG to ATG, facilitating expression in *E. coli*.

Example 2

Screening *A. facilis* 72W Nitrilase Random Mutagenesis Libraries for Increased Nitrilase Activity Approximately 5,000 colonies from each of the error-prone PCR libraries were plated on LB agar supplemented with 50 mg/L ampicillin. High throughput screening was performed in 96-well microtiter plates using robotics. After growth of individual colonies in liquid LB supplemented with 50 mg/L ampicillin and 1 mM IPTG for 18 h at 37° C., 200 rpm shaking, cultures were supplied with 10 mM 3-hydroxyvaleronitrile (3-HVN) for 1 h at 37° C., 80 Hz linear shaking. Reactions were stopped by filtering out the bacteria, and supernatants to be analyzed were sealed in microtiter plates and stored at 4° C. until analysis. Production of 3-hydroxyvaleric acid (3-HVA) was measured by mass spectrometry (APCI-MRM, mobile phase 95% MeOH/ 5% $H_2O$ at 5 mL/min; needle wash 50% MeOH/50% $H_2O$ at 4 mL/min per needle). Three clones demonstrating 3-HVN conversion that exceeded the control (*E.coli* TOP10/ pNM18) by approximately 5-fold and were identified and designated *E.coli* TOP10/pNM18/B4, *E. coli* TOP10/ pNM18/B2 and *E. coli* TOP10/pNM18/H9.

Example 3

Assay of *E. coli* TOP10/pNM18 (Control), *E. coli* TOP10/pNM18/B4, *E. coli* TOP10/pNM18/B2 and *E. coli* TOP10/pNM18/H9 for Nitrilase Activity Inoculum was prepared by adding 50 mL of LB media containing 50 mg/L ampicillin to sterile 125 mL flasks, then scraping frozen cell stock into the flask and incubating the resulting mixture at 37° C. and 200 rpm for 12 to 16 h. The optical density of the resulting culture was recorded, then 80% glycerol in water was added to a final concentration of 15% (v/v), and 14.3 mL aliquots of the resulting inoculum added to 50-mL centrifuge tubes and stored frozen at −80° C. until used. To a 4-L sterile flask was added 1.80 L of LB broth, 0.9 mL of an aqueous solution of ampicillin (100 mg/mL) and 1.8 mL of an aqueous solution of IPTG (1.0 M). To the flask was then added 87.5 mL of *E. coli* TOP10/ pNM18 (control), *E. coli* TOP10/pNM18/B4, *E. coli* TOP10/pNM18/B2 or *E. coli* TOP10/pNM18/H9 inoculum, the contents of the flask mixed, and 250-mL aliquots of the resulting mixture transferred to each of six sterile 1-L flasks. The cultures were incubated at 37° C. with rotary mixing at 200 rpm for 8 h, and the cells from each flask collected by centrifugation at 4° C. and stored frozen at −80° C.

To a 4-mL glass vial equipped with a magnetic stir bar was added 1.0 mL of 1.0 M 3-hydroxyvaleronitrile in water, and the vial and its contents equilibrated to 25° C. in a temperature controlled water bath. With stirring, 1.0 mL of 0.100 M potassium phosphate buffer (pH 7.0) containing 400 mg wet cell paste pre-equilibrated to 25° C. was added to the vial. Samples (0.100 mL) were taken at predetermined times and mixed with a solution comprised of 0.100 mL water, 0.020 mL of 6.0 N acetic acid and 0.200 mL of 0.20 M sodium butyrate in water (HPLC external standard). The resulting mixture was centrifuged and the resulting supernatant analyzed by HPLC for 3-hydroxyvaleric acid using a Supelco LC-18-DB column (15 cm×4.6 mm): mobile phase: aqueous 10 mM sodium acetate (NaOAc), 10 mM acetic acid (AcOH), 7.5% (v/v) methanol. The dry cell weight (dcw) of each cell paste used in the assay was used to determine the nitrilase activity of E. coli TOP10/pNM18 (Table 1), E. coli TOP10/pNM18/B4 (Table 2), E. coli TOP10/pNM18/B2 (Table 3), and E. coli TOP10/pNM18/H9 (Table 4), based on the rate of production of 3-hydroxyvaleric acid. A comparison of the relative nitrilase activity of E. coli TOP10/pNM18 (control), E. coli TOP10/pNM18/B4, E. coli TOP10/pNM18/B2, and E. coli TOP10/pNM18/H9 is presented in Table 5.

TABLE 1

E. coli TOP10/pNM18 Nitrilase Activity (Control)

| flask | OD (600 nm) 0 h | OD (600 nm) 8 h | 3-HVN U/g dry cell wt. |
|---|---|---|---|
| TOP10/pNM18-1 | 0.080 | 2.25 | 2.00 |
| TOP10/pNM18-2 | 0.081 | 2.19 | 2.20 |
| TOP10/pNM18-3 | 0.083 | 2.28 | 2.07 |
| TOP10/pNM18-4 | 0.082 | 2.29 | 1.96 |
| TOP10/pNM18-5 | 0.085 | 2.23 | 2.13 |
| TOP10/pNM18-6 | 0.081 | 2.19 | 2.11 |
| TOP10/pNM18 (average) | | | 2.08 |

TABLE 2

E. coli TOP10/pNM18/B4 Nitrilase Activity

| flask | OD (600 nm) 0 h | OD (600 nm) 8 h | 3-HVN U/g dry cell wt. |
|---|---|---|---|
| TOP10/pNM18/B4-1 | 0.067 | 1.88 | 3.75 |
| TOP10/pNM18/B4-2 | 0.078 | 2.05 | 3.78 |
| TOP10/pNM18/B4-3 | 0.075 | 1.88 | 3.69 |
| TOP10/pNM18/B4-4 | 0.080 | 1.84 | 3.83 |
| TOP10/pNM18/B4-5 | 0.080 | 1.98 | 3.69 |
| TOP10/pNM18/B4-6 | 0.085 | 1.79 | 3.25 |
| TOP10/pNM18/B4 (average) | | | 3.67 |

TABLE 3

E. coli TOP10/pNM18/B2 Nitrilase Activity

| flask | OD (600 nm) 0 h | OD (600 nm) 8 h | 3-HVN U/g dry cell wt. |
|---|---|---|---|
| TOP10/pNM18/B2-1 | 0.086 | 1.82 | 13.62 |
| TOP10/pNM18/B2-2 | 0.073 | 1.89 | 11.47 |
| TOP10/pNM18/B2-3 | 0.088 | 2.13 | 12.83 |
| TOP10/pNM18/B2-4 | 0.078 | 2.13 | 10.51 |
| TOP10/pNM18/B2-5 | 0.085 | 2.13 | 11.67 |
| TOP10/pNM18/B2-6 | 0.083 | 1.78 | 11.82 |
| TOP10/pNM18/B2 (average) | | | 12.0 |

TABLE 4

E. coli TOP10/pNM18/H9 Nitrilase Activity

| flask | OD (600 nm) 0 h | OD (600 nm) 8 h | 3-HVN U/g dry cell wt. |
|---|---|---|---|
| TOP10/pNM18/H9-1 | 0.095 | 2.89 | 16.32 |
| TOP10/pNM18/H9-2 | 0.074 | 2.56 | 15.62 |
| TOP10/pNM18/H9-3 | 0.090 | 2.51 | 15.84 |
| TOP10/pNM18/H9-4 | 0.090 | 2.44 | 15.41 |
| TOP10/pNM18/H9-5 | 0.100 | 2.46 | 14.41 |
| TOP10/pNM18/H9-6 | 0.085 | 4.63 | 14.87 |
| TOP10/pNM18/H9 (average) | | | 15.4 |

TABLE 5

Summary of Nitrilase Activity for TOP10/pNM18 Mutants

| strain | 3-HVN U/g dry cell wt. | Nitrilase activity relative to TOP10/pNM18 |
|---|---|---|
| TOP10/pNM18 (control) | 2.08 | 1.0 |
| TOP10/pNM18/B4 | 3.67 | 1.8 |
| TOP10/pNM18/B2 | 12.0 | 5.8 |
| TOP10/pNM18/H9 | 15.4 | 7.4 |

Example 4

Identification of Mutations in A. facilis 72W Nitrilase Conferring Increased Nitrilase Activity Nucleotide sequence analysis was used to determine the mutations present in each of the 3 clones having increased nitrilase activity (TOP10/pNM18/B4, TOP10/pNM18/B2, and TOP10/pNM18/H9), and the corresponding amino acid changes were deduced. Compared to the TOP10/pNM18 control (SEQ ID NOs:3 and 4), TOP10/pNM18/B2 and TOP10/pNM18/H9 (SEQ ID NOs:5 and 6), which are identical, have one amino acid change (Thr210 to Ala; T210A), and TOP10/pNM18/B4 (SEQ ID NOs:7 and 8) has 3 amino acid changes (Tyr65 to Cys (Y65C); Phe174 to Ile (F174I); and Thr210 to Ile (T210I)). None of these changes are contained within the catalytic domain of this enzyme, or within generally-conserved regions among numerous nitrilase enzymes, suggesting that there was no way to predict a priori that changes at these particular residues could produce improvement in nitrilase activity. None of these changes had any detectable effect on nitrilase protein production, as quantified by laser densitometry analysis of the SDS-PAGE gel(s).

Example 5

Saturation Mutagenesis at Threonine Residue 210

The threonine residue at position 210 of the 72W nitrilase enzyme was changed to each of the other 19 amino acids using the QuikChange Site-Directed Mutagenesis Kit (Stratagene, La Jolla, Calif.). Degenerate oligonucleotides were used according to the manufacturer's instructions, and identification of the resulting codon changes were determined by nucleotide sequencing. Any codon changes not obtained by this method were made by using non-degenerate oligonucleotides incorporating the specific codon change desired. For example, 210Met (T210M) was obtained using primers (underlined nucleotides indicate the new codon) identified as SEQ ID NO:9 (5'-CGAAGCCAACGCGACGGTC ATGCGCTCGTACGCAATCGAAGG-3') and SEQ ID NO:10 (5'-CCTTCGATTGCGTACGAGCG CATGACCGTCGCGTTGGCTTCG-3').

Nitrilase activity was measured from all 20 enzyme variants. In addition to the previously identified 210Ala (T210A) improvement (Examples 3 and 4), increased activity relative to the control (pNM18) was observed for 210Cys (T210C; SEQ ID NOs:11 and 12) (Tables 6 and 7). The 210Cys change had no detectable effect on nitrilase protein production, as determined by SDS-PAGE analysis. We found no other changes at residue 210 that produced improvement in nitrilase activity; some changes had no effect (for example, 210Val (T210V)) and some changes had detrimental effects (for example, 210Gly (T210G)) on nitrilase activity. These results suggest that there was no way of predicting a priori the effect of any given mutation at residue 210.

TABLE 6

E. coli TOP10/pNM18/210Cys Nitrilase Activity

| Flask | OD (600 nm) 0 h | OD (600 nm) 8 h | 3-HVN U/g dry cell wt. |
|---|---|---|---|
| TOP10/pNM18/210Cys-1 | 0.075 | 2.09 | 9.98 |
| TOP10/pNM18/210Cys-2 | 0.086 | 2.07 | 11.79 |
| TOP10/pNM18/210Cys-3 | 0.079 | 2.34 | 11.35 |
| TOP10/pNM18/210Cys-4 | 0.083 | 2.08 | 11.57 |
| TOP10/pNM18/210Cys-5 | 0.090 | 2.28 | 9.81 |
| TOP10/pNM18/210Cys-6 | 0.085 | 2.16 | 11.09 |
| TOP10/pNM18/210Cys (average) | | | 10.97 |

TABLE 7

Summary of Nitrilase Activity for 210Cys Mutant

| Strain | 3-HVN U/g dcw | relative nitrilase activity |
|---|---|---|
| TOP10/pNM18 (control) | 1.77 | 1.0 |
| TOP10/pNM18/210Cys | 11.0 | 6.2 |

Example 6

Immobilization of E. coli TOP10/pNM18 Cells (Control) or E. coli TOP10/pNM18/H9 Cells in Calcium-crosslinked Alginate To a 4.0-L sterile flask was added 1.80 L of LB broth, 0.9 mL of an aqueous solution of ampicillin (100 mg/mL) and 1.8 mL of an aqueous solution of IPTG (1.0 M). To the flask was then added 87.5 mL of E. coli TOP10/pNM18 (control) or E. coli TOP10/pNM18/H9 inoculum, the contents of the flask mixed, and 250-mL aliquots of the resulting mixture transferred to each of seven sterile 1-L flasks. The cultures were incubated at 37° C. with rotary mixing at 200 rpm for 8 h, the resulting cell suspensions combined, and the cells collected by centrifugation at 4° C. and stored frozen at −80° C. For E. coli TOP10/pNM18 (control), the mean initial OD at 600 nm was 0.133 AU, and the mean final OD after 8 h was 2.13 AU, producing ca. 6 g cell paste. For E. coli TOP10/pNM18/H9, the mean final OD was 1.68 AU, producing ca. 5 g cell paste.

Into a 100-mL media bottle equipped with magnetic stir bar and containing 7.46 g of distilled, deionized water at 50° C. was slowly added 0.413 g of FMC BioPolymer Protanal® LF 10/60 alginate with rapid stirring. The mixture was heated to 75–80° C. with rapid stirring until the alginate was completely dissolved, and the resulting solution cooled to 25° C. in a water bath. To the alginate suspension was added with stirring either 4.75 g of E. coli (pNM18) wet cell paste (23.7% dry cell weight) and 2.37 mL of distilled water, or 4.97 g of E. coli (pNM18/H9) wet cell paste (22.6% dry cell weight) and 2.15 mL of distilled water. The cell/alginate mixture was added dropwise by syringe to 80 mL of 0.20 M calcium acetate buffer (pH 7.0) at 25° C. with stirring. After stirring for 2 h, the buffer was decanted from the resulting beads, which were resuspended in 30 mL of 0.20 M calcium acetate buffer (pH 7.0) at 25° C. With stirring, 0.61 g of 25 wt % glutaraldehyde (GA) in water was added and the beads mixed for 1.0 h at 25° C. To the suspension was then added 2.42 g of 12.5 wt % polyethylenimine (PEI) (BASF Lupasol® PR971L, average molecular weight ca. 750,000) in water, and the beads mixed for an additional 1 h at 25° C. The crosslinked beads were then washed twice with 30 mL of 5 mM calcium acetate buffer (pH 7.0) at 25° C., and stored in an aqueous buffer containing 1.0 M ammonium acetate, 4 mM calcium acetate and 10 mM ammonium bicarbonate (pH7.1) at 5° C.

Example 7

Comparison of Alginate-immobilized E. coli TOP10/pNM18/H9 or E. coli TOP10/pNM18 (Control) as Catalyst for Hydrolysis of 3 -Hydroxyvaleronitrile Into a 50-mL jacketed reaction vessel equipped with an overhead stirrer (temperature-controlled at 35° C. with a recirculating temperature bath) was placed 6.0 g of GA/PEI-crosslinked E. coli TOP10/pNM18 cell/alginate beads (control) prepared as described in Example 6. To the reaction vessel was added 13.4 mL of distilled, deionized water, 0.2 mL of 0.20 M calcium acetate buffer (pH 7.0, 2.0 mM final calcium ion concentration in reaction mixture) and 0.40 mL (0.386 g) of 3-hydroxyvaleronitrile (0.400 M total concentration), and the mixture stirred at 35° C. Samples (0.200 mL) were mixed with 0.200 mL of 200 mM sodium butyrate (HPLC external standard), and the supernatant analyzed by HPLC. After 25 h, the conversion of 3-HVN was 100%, and the yield of 3-HVA was 100%. The nitrilase activity of the E. coli TOP10/pNM18 cell/alginate bead catalyst (control) was 0.449 3-HVN U/g bead.

The reaction described immediately above was repeated, except that the catalyst was 6.0 g of GA/PEI-crosslinked E. coli TOP10/pNM18/H9 cell/alginate beads, prepared as described in Example 6. After 19 h, the conversion of 3-HVN was 100%, and the yield of 3-HVA was 100%. The nitrilase activity of the E. coli TOP10/pNM18/H9 cell/alginate bead catalyst was 2.85 3-HVN U/g bead (a 6.35-fold improvement versus control). At the end of the reaction, the product mixture was decanted from the catalyst beads, and an additional 13.3 mL of distilled, deionized water, 0.2 mL of 0.20 M calcium acetate buffer (pH 7.0, 2.0 mM final calcium ion concentration in reaction mixture) and 0.40 mL (0.386 g) of 3-hydroxyvaleronitrile (0.400 M total concentration) was mixed with the immobilized-cell catalyst at 35° C. After 20 h, the conversion of 3-HVN was 100%, and the yield of 3-HVA was 100%. The nitrilase activity of the catalyst was 2.99 U/g bead. This recycle procedure was repeated for a total of twenty-one consecutive reactions, and the nitrilase activity and percent recovered activity of the catalyst for each reaction is listed in Table 11. For reaction 21 (Table 8), the conversion of 3-HVN was 100%, and the yield of 3-HVA was 100% after 20 h, and the nitrilase activity of the catalyst was 81% of the initial catalyst activity.

TABLE 8

Nitrilase Activity and Percent Recovered Catalyst Activity for GA/PEI-crosslinked E. coli TOP10/pNM18/H9 Cell/alginate Beads in 0.40 M 3-HVN Reactions at 35° C.

| rxn # | 3-HVN U/g catalyst bead | percent recovery |
|---|---|---|
| 1 | 2.85 | — |
| 2 | 2.99 | 105 |
| 3 | 2.59 | 91 |
| 4 | 3.75 | 130 |
| 5 | 3.45 | 121 |
| 6 | 3.07 | 109 |
| 7 | 3.09 | 109 |
| 8 | 3.33 | 116 |
| 9 | 2.97 | 105 |
| 10 | 2.82 | 98 |
| 11 | 2.98 | 105 |
| 12 | 3.13 | 109 |
| 13 | 2.83 | 98 |
| 14 | 2.77 | 98 |
| 15 | 2.81 | 98 |
| 16 | 2.67 | 95 |
| 17 | 2.68 | 95 |
| 18 | 2.50 | 88 |
| 19 | 2.49 | 88 |
| 21 | 2.34 | 81 |

Example 8

Construction and Fermentation of *Escherichia coli* FM5/pNM18 (Control) and FM5/pNM18/H9 Cells

*E. coli* strain FM5 (ATCC 53911) was independently transformed with plasmids pNM18 (Example 1) and pNM18/H9 (Example 2) using the calcium chloride procedure well-known in the art.

The production of nitrilase in a 14-L Braun Biostat C fermentor (B. Braun Biotech International Gmbh, Melsungen, Germany) was made in mineral medium with glucose, ammonia, yeast extract and salts. *E. coli* strains FM5/pNM18 (control) and FM5/pNM18/H9 harboring plasmids pNM18 and pNM18/H9 respectively (as described in Examples 1 and 2) were grown in a seed culture for 10–20 h prior to inoculation of the fermentor. IPTG was added at specified time and cells were harvested 24 h after IPTG addition.

Fermentation protocol: vessel medium was prepared in an initial batch of 7.5 L containing 80 g Yeast Extract, 160 g caseamino acids, 8.0 g $MgSO_4 \cdot 7H_2O$, 8.0 g $(NH_4)_2SO_4$, and 10 mL Mazu DF204 antifoam (BASF Corporation, Mount Olive, N.J.). Following sterilization, 369 g glucose solution (60% w/w), 160 mL trace element solution (Table 9), 200 mL $PO_4$ solution (21.0 g of $K_2HPO_4$ and 11.0 g of $KH_2PO_4$ in 200 mL of $diH_2O$ adjusted pH to 6.8 Steam sterilized) and 100 mg/L ampicillin were added. $NH_4OH$ (40% w/v) and 20% w/v $H_2PO_4$ were used for pH control. The set points for agitation, aeration, pH, pressure, dissolved oxygen concentration (DO), and temperature are described in Table 10 below. The dissolved oxygen concentration was controlled at 25% of air saturation with the agitation to rise first with increase oxygen demand and the aeration to follow.

The 500 mL seed culture was grown in a 2-L flask at 36° C., 300 rpm for 10–20 h to an $OD_{\lambda=550}$ of >2.0. In the fermentor at culture densities of 20–30 OD additional AMP was added to 100 mg/L. IPTG was added to 0.1 mM for FM5/pNM18 (control) and 1 mM for FM5/pNM18/H9 at 35–40 $OD_{\lambda=550}$ for FM5/pNM18 and 20–30 $OD_{\lambda=550}$ for FM5/pNM18/H9. Glucose feed was started at <5 g/L and the scheduled rates are described in Table 11. Glucose feed rate was reduced if glucose accumulated above 2 g/L. Twenty four hours after IPTG addition the cells were chilled to 5–10° C. and harvested by centrifugation.

TABLE 9

Trace Elements Solution

| Chemical | Concentration |
|---|---|
| Citric acid | 10 g/L |
| $CaCl_2 \cdot 2H_2O$ | 1.5 g/L |
| $FeSO_4 \cdot 7H_2O$ | 5 g/L |
| $ZnSO_4 \cdot 7H_2O$ | 0.39 g/L |
| $CuSO_4 \cdot 5H_2O$ | 0.38 g/L |
| $CoCl_2 \cdot 6H_2O$ | 0.2 g/L |
| $MnCl_2 \cdot 4H_2O$ | 0.3 g/L |

TABLE 10

Fermentation Run Conditions

| | Initial Set-Point | Minimum | Maximum |
|---|---|---|---|
| Stirrer (rpm) | 400 | 400 | 850 |
| Airflow (slpm) | 2 | 2 | 16 |
| pH | 6.8 | 6.8 | 6.8 |
| Pressure (kPa) | 3.45 | 3.45 | 3.45 |
| DO | 25% | 25% | 25% |
| Temperature ° C. | 36 | 36 | 36 |

TABLE 11

Glucose Feed Protocol

| Time (h) | Rate (g/min) |
|---|---|
| 0–4 | 0.27 |
| 4–16 | 0.55 |
| 16–End | 0.42 |

The *E. coli* FM5 transformants were assayed for 3-HVN nitrilase activity as described in Example 3. The nitrilase activities of the *E. coli* FM5 strains produced in the duplicate fermentation runs are listed in Table 12, below, and compared to the nitrilase activities of *A. facilis* 72W and *E. coli* SS1001 (ATCC PTA-1177; WO 01/75077). The nitrilase catalyst improvement (previously described) for *E. coli* SS1001 as compared to *A. facilis* 72W is attributed to improved nitrilase enzyme expression. In contrast, the significant improvement demonstrated for *E. coli* FM5/pNM18/H9 as compared to *E. coli* FM5/pNM18 (control) is attributed to improved nitrilase enzyme activity resulting from modifications in enzyme structure. In addition to the approximate 5.5-fold improvement in nitrilase activity of *E. coli* FM5/pNM18/H9 compared to *E. coli* FM5/pNM18 (control), it is noteworthy that nitrilase activity of *E. coli* FM5/pNM18/H9 is also about 4.2-fold greater than that of *E. coli* SS1001.

TABLE 12

Comparison of 3-HVN Nitrilase Activity of E. coli FM5
Strains to A. facilis 72W and E. coli SS1001.

| strain | 3-HVN U/g dcw |
|---|---|
| A. facilis 72W | 3.2 |
| E. coli SS1001 | 7.6 |
| E. coli FM5/pNM18-run1 (control) | 5.98 |
| E. coli FM5/pNM18-run2 (control) | 5.55 |
| E. coli FM5/pNM18/H9-run1 | 31.3 |
| E. coli FM5/pNM18/H9-run2 | 31.8 |

Example 9

Comparison of Nitrilase Activities of *E. coli* TOP10/pNM18 (Control) and *E. coli* TOP10/pNM18/H9 for Hydrolysis of 3-HBN and 3-HVN The preparation of *E. coli* TOP10/pNM18 (control) and *E. coli* TOP10/pNM18/H9 was repeated according to the procedures described in Example 3, and the resulting cells were assayed for nitrilase activity (Table 13) for hydrolysis of 0.5 M 3-hydroxyvaleronitrile (3-HVN) or 0.5 M 3-hydroxybutyronitrile (3-HBN), as described in Example 3. The nitrilase activity of *E. coli* TOP10/pNM18/H9 for 3-HBN was ca. 1.9-fold relative to *E. coli* TOP10/pNM18 (control).

TABLE 13

Nitrilase Activities of E. coli TOP10/pNM18 (control) and E. coli
TOP10/pNM18/H9 for Hydrolysis of 3-HBN and 3-HVN

| strain | substrate (0.5 M) | U/g dry cell wt. |
|---|---|---|
| E. coli TOP10/pNM18 (control) | 3-HVN | 1.94 |
| E. coli TOP10/pNM18 (control) | 3-HBN | 2.69 |
| E. coli TOP10/pNM18/H9 | 3-HVN | 14.0 |
| E. coli TOP10/pNM18/H9 | 3-HBN | 5.2 |

Example 10

Targeted Saturation Mutagenesis of the 72W Nitrilase Catalytic Domain

Saturation mutagenesis within the *A. facilis* 72W nitrilase (SEQ ID NO:4) catalytic domain(160G 161G 162L 163N 164C 165W 166E 167H 168F 169Q 170P 171L 172S 173K) of those residues not universally conserved among known bacterial nitrilases (underlined) was completed using degenerate oligonucleotides and the QuikChange Site-Directed Mutagenesis Kit (Stratagene, La Jolla, Calif.) according to the manufacturer's instructions. Specifically, nine mini-libraries (500–1000 colonies) were constructed, one for each of the active site residues targeted. These libraries were screened for increased 3-HVN nitrilase activity as previously described (Example 2). Eleven clones (all from mini-library of 168F (Phe168)) were identified, each clone demonstrating 3-HVA production that exceeded the control (pNM18) by approximately 2–3 fold. Nucleotide sequencing was used to determine the specific codon changes conferring the increased nitrilase activity (Table 14). Although nitrilase activities were not measured directly, SDS-PAGE analysis determined that substantially equal levels of nitrilase protein was produced from each mutant. Therefore, it is concluded that the increased production of 3-HVA from the mutants is attributable to increased nitrilase activity of the enzyme.

TABLE 14

Summary of Residue 168 Saturation Mutagenesis Improvements

| Residue 168 amino acid | mM/hr 3-HVA | fold increase |
|---|---|---|
| Phe (control) | 0.55 | — |
| Lys (SEQ ID NOs: 13 and 14) | 1.38 (n = 3) | 2.5 |
| Val (SEQ ID NOs: 15 and 16) | 1.39 (n = 6) | 2.5 |
| Leu (SEQ ID NOs: 17 and 18) | 1.34 (n = 2) | 2.4 |

What is claimed is:

1. An isolated nucleic acid molecule encoding an enzymatically-active polypeptide having the amino acid sequence of SEQ ID NO:4; said isolated nucleic acid molecule further comprising at least one mutation that results in at least one amino acid substitution of SEQ ID NQ:4, selected from the group consisting of:
   a) a substitution at position 210 with alanine, isoleucine, or cysteine;
   b) a substitution at position 65 with cysteine;
   c) a substitution at position 168 with lysine, valine or leucine; and
   d) a substitution at position 174 with isoleucine,
wherein said nucleic acid molecule encodes a polypeptide having nitrilase activity at least 1.8-fold higher relative to the activity of the *A. facilis* 72W (ATCC 55746) nitrilase when converting 3-hydroxyvaleronitrile to 3-hydroxyvaleric acid under identical reaction conditions.

2. The isolated nucleic acid molecule of claim 1, having a nucleic acid sequence seiected from the group consisting of SEQ ID NOs:5, 7, 11, 13, 15, and 17.

3. The isolated nucleic acid molecule of claim 1, encoding an amino acid sequence selected from the group consisting of SEQ ID NOs: 6, 8, 12, 14, 16 and 18.

4. A chimeric gene comprising the isolated nucleic acid molecule of claims 1, 2, or 3, operably linked to a suitable regulatory sequence.

5. An expression cassette comprising the chimeric gene of claim 4.

6. A transformed microorganism comprising the chimeric gene of claim 4.

7. A transformed microorganism comprising the expression cassette of claim 5.

8. The transformed microorganism of claim 6 wherein the microorganism is selected from the group consisting of *Comamonas* sp., *Corynebacterium* sp., *Brevibacterium* sp., *Rhodococcus* sp., *Azotobacter* sp., *Citrobacter* sp., *Enterobacter* sp., *Clostridium* sp., *Klebsiella* sp., *Salmonella* sp., *Lactobacillus* sp., *Aspergillus* sp., *Saccharomyces* sp., *Zygosaccharomyces* sp., *Pichia* sp., *Kluyveromyces* sp., *Candida* sp., *Hansenula* sp., *Dunaliella* sp., *Debaryomyces* sp., *Mucor* sp., *Torulopsis* sp., *Methylobacteria* sp., *Bacillus* sp., *Escherichia* sp., *Pseudomonas* sp., *Rhizobium* sp., and *Streptomyces* sp.

9. The transformed microorganism of claim 8 wherein the transformed microorganism is an *Escherichia coli* strain selected from the group consisting of MG1655 (ATCC 47076), FM5 (ATCC 53911), W3110 (ATCC 27325), MC4100 (ATCC 35695). and W1485 (ATCC 12435).

* * * * *